US012408869B2

United States Patent
Al-Ali et al.

(10) Patent No.: US 12,408,869 B2
(45) Date of Patent: Sep. 9, 2025

(54) DISPOSABLE COMPONENTS FOR REUSABLE PHYSIOLOGICAL SENSOR

(71) Applicant: Masimo Corporation, Irvine, CA (US)

(72) Inventors: Ammar Al-Ali, San Juan Capistrano, CA (US); Marcelo Lamego, Cupertino, CA (US); Jim Litchfield, Singapore (SG); Gregory A. Olsen, Lake Forest, CA (US)

(73) Assignee: Masimo Corporation, Irvine, CA (US)

( * ) Notice: Subject to any disclaimer, the term of this patent is extended or adjusted under 35 U.S.C. 154(b) by 677 days.

(21) Appl. No.: 17/656,982

(22) Filed: Mar. 29, 2022

(65) Prior Publication Data

US 2022/0218284 A1     Jul. 14, 2022

Related U.S. Application Data

(63) Continuation of application No. 16/425,592, filed on May 29, 2019, now Pat. No. 11,331,042, which is a (Continued)

(51) Int. Cl.
*A61B 5/1455*     (2006.01)
*A61B 5/00*     (2006.01)
(Continued)

(52) U.S. Cl.
CPC .......... *A61B 5/6838* (2013.01); *A61B 5/0205* (2013.01); *A61B 5/02444* (2013.01);
(Continued)

(58) Field of Classification Search
None
See application file for complete search history.

(56) References Cited

U.S. PATENT DOCUMENTS 3,463,142 A     8/1969    Harte
3,647,299 A     3/1972    Lavallee
(Continued)

FOREIGN PATENT DOCUMENTS

AU     200010929     5/2000
CA     2 346 639     4/2000
(Continued)

OTHER PUBLICATIONS

US 2024/0016391 A1, 01/2024, Lapotko et al. (withdrawn)
(Continued)

*Primary Examiner* — Marjan Fardanesh
(74) *Attorney, Agent, or Firm* — Knobbe, Martens, Olson & Bear, LLP

(57) ABSTRACT

A sensor cartridge according to embodiments of the disclosure is capable of being used with a non-invasive physiological sensor. Certain embodiments of the sensor cartridge protect the sensor from damage, such as damage due to repeated use, reduce the need for sensor sanitization, or both. Further, embodiments of the sensor cartridge are positionable on the user before insertion in the sensor and allow for improved alignment of the treatment site with the sensor. In addition, the sensor cartridge of certain embodiments of the disclosure can be configured to allow a single sensor to comfortably accommodate treatment sites of various sizes such as for both adult and pediatric applications.

9 Claims, 13 Drawing Sheets

Related U.S. Application Data continuation of application No. 15/864,389, filed on Jan. 8, 2018, now Pat. No. 10,342,487, which is a continuation of application No. 14/626,570, filed on Feb. 19, 2015, now Pat. No. 9,895,107, which is a continuation of application No. 12/782,651, filed on May 18, 2010, now Pat. No. 8,989,831.

(60) Provisional application No. 61/179,670, filed on May 19, 2009.

(51) Int. Cl.
    *A61B 5/0205* (2006.01)
    *A61B 5/024* (2006.01)
    *A61B 46/10* (2016.01)
    *A61B 46/20* (2016.01)

(52) U.S. Cl.
    CPC ........ *A61B 5/14552* (2013.01); *A61B 5/6826* (2013.01); *A61B 46/10* (2016.02); *A61B 46/20* (2016.02); *A61B 5/024* (2013.01); *A61B 2046/201* (2016.02); *A61B 2560/0285* (2013.01); *A61B 2562/247* (2013.01)

(56) References Cited

U.S. PATENT DOCUMENTS

| | | |
|---|---|---|
| 3,740,570 A | 6/1973 | Kaelin et al. |
| 3,799,672 A | 3/1974 | Vurek |
| 4,086,915 A | 5/1978 | Kofsky et al. |
| 4,169,976 A | 10/1979 | Cirri |
| 4,182,977 A | 1/1980 | Stricklin, Jr. |
| 4,308,456 A | 12/1981 | Van Der Gaag et al. |
| 4,346,590 A | 8/1982 | Brown |
| 4,407,290 A | 10/1983 | Wilber |
| 4,449,821 A | 5/1984 | Lee |
| 4,480,886 A | 11/1984 | Bergamin |
| 4,580,867 A | 4/1986 | Wright et al. |
| 4,621,643 A | 11/1986 | New, Jr. et al. |
| 4,653,498 A | 3/1987 | New, Jr. et al. |
| 4,685,464 A | 8/1987 | Goldberger et al. |
| 4,700,708 A | 10/1987 | New, Jr. et al. |
| 4,770,179 A | 9/1988 | New, Jr. et al. |
| 4,825,872 A | 5/1989 | Tan |
| 4,830,014 A | 5/1989 | Goodman et al. |
| 4,848,901 A | 7/1989 | Hood, Jr. |
| 4,865,038 A | 9/1989 | Rich et al. |
| 4,877,322 A | 10/1989 | Hill |
| 4,913,150 A | 4/1990 | Cheung et al. |
| 4,942,877 A | 7/1990 | Sakai et al. |
| 4,960,128 A | 10/1990 | Gordon et al. |
| 4,964,408 A | 10/1990 | Hink et al. |
| 4,974,591 A | 12/1990 | Awazu et al. |
| 5,041,187 A | 8/1991 | Hink et al. |
| 5,058,588 A | 10/1991 | Kaestle |
| 5,069,213 A | 12/1991 | Hink et al. |
| 5,090,410 A | 2/1992 | Saper et al. |
| 5,094,240 A | 3/1992 | Muz |
| 5,113,862 A | 5/1992 | Mortazavi |
| 5,140,228 A | 8/1992 | Biegel |
| 5,158,323 A | 10/1992 | Yamamoto et al. |
| 5,163,438 A | 11/1992 | Gordon et al. |
| 5,170,786 A | 12/1992 | Thomas et al. |
| 5,209,230 A | 5/1993 | Swedlow et al. |
| 5,226,417 A | 7/1993 | Swedlow et al. |
| 5,246,003 A | 9/1993 | DeLonzor |
| 5,249,576 A | 10/1993 | Goldberger et al. |
| 5,267,562 A | 12/1993 | Ukawa et al. |
| 5,273,041 A | 12/1993 | Richards et al. |
| 5,279,295 A | 1/1994 | Martens et al. |
| 5,287,853 A | 2/1994 | Vester et al. |
| 5,308,919 A | 5/1994 | Minnich |
| 5,311,865 A | 5/1994 | Mayeux |
| 5,319,355 A | 6/1994 | Russek |
| 5,337,744 A | 8/1994 | Branigan |
| 5,339,810 A | 8/1994 | Ivers et al. |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| 5,387,122 A | 2/1995 | Goldberger et al. |
| 5,397,247 A | 3/1995 | Aoki et al. |
| D359,546 S | 6/1995 | Savage et al. |
| 5,431,170 A | 7/1995 | Mathews |
| 5,436,499 A | 7/1995 | Namavar et al. |
| D361,840 S | 8/1995 | Savage et al. |
| 5,437,275 A | 8/1995 | Amundsen et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,460,182 A | 10/1995 | Goodman et al. |
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,507,286 A | 4/1996 | Solenberger |
| 5,520,177 A | 5/1996 | Ogawa et al. |
| 5,533,511 A | 7/1996 | Kaspari et al. |
| 5,534,851 A | 7/1996 | Russek |
| 5,561,275 A | 10/1996 | Savage et al. |
| 5,562,002 A | 10/1996 | Lalin |
| 5,579,373 A | 11/1996 | Jang |
| 5,590,649 A | 1/1997 | Caro et al. |
| 5,602,924 A | 2/1997 | Durand et al. |
| 5,619,992 A | 4/1997 | Guthrie et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,660,567 A | 8/1997 | Nierlich et al. |
| 5,664,270 A | 9/1997 | Bell et al. |
| 5,671,914 A | 9/1997 | Kalkhoran et al. |
| 5,673,693 A | 10/1997 | Solenberger |
| 5,678,544 A | 10/1997 | DeLonzor et al. |
| 5,685,299 A | 11/1997 | Diab et al. |
| 5,726,440 A | 3/1998 | Kalkhoran et al. |
| D393,830 S | 4/1998 | Tobler et al. |
| 5,740,019 A | 4/1998 | Lee |
| 5,743,262 A | 4/1998 | Lepper, Jr. et al. |
| 5,747,806 A | 5/1998 | Khalil et al. |
| 5,750,994 A | 5/1998 | Schlager |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,786,592 A | 7/1998 | Hök |
| 5,791,347 A | 8/1998 | Flaherty et al. |
| 5,810,724 A | 9/1998 | Gronvall |
| 5,810,734 A | 9/1998 | Caro et al. |
| 5,817,008 A | 10/1998 | Rafert et al. |
| 5,817,010 A | 10/1998 | Hibl |
| 5,823,950 A | 10/1998 | Diab et al. |
| 5,830,131 A | 11/1998 | Caro et al. |
| 5,833,618 A | 11/1998 | Caro et al. |
| RE36,000 E | 12/1998 | Swedlow et al. |
| 5,860,919 A | 1/1999 | Kiani-Azarbayjany et al. |
| 5,879,373 A | 3/1999 | Röper et al. |
| 5,890,929 A | 4/1999 | Mills et al. |
| 5,904,654 A | 5/1999 | Wohltmann et al. |
| 5,910,108 A | 6/1999 | Solenberger |
| 5,919,133 A | 7/1999 | Taylor et al. |
| 5,919,134 A | 7/1999 | Diab |
| 5,934,925 A | 8/1999 | Tobler et al. |
| 5,940,182 A | 8/1999 | Lepper, Jr. et al. |
| 5,987,343 A | 11/1999 | Kinast |
| 5,991,648 A | 11/1999 | Levin |
| 5,995,855 A | 11/1999 | Kiani et al. |
| 5,997,343 A | 12/1999 | Mills et al. |
| 5,999,834 A | 12/1999 | Wang et al. |
| 6,002,952 A | 12/1999 | Diab et al. |
| 6,010,937 A | 1/2000 | Karam et al. |

(56) References Cited

U.S. PATENT DOCUMENTS

| | | |
|---|---|---|
| 6,011,986 A | 1/2000 | Diab et al. |
| 6,014,576 A | 1/2000 | Raley |
| 6,027,452 A | 2/2000 | Flaherty et al. |
| 6,036,642 A | 3/2000 | Diab et al. |
| 6,040,578 A | 3/2000 | Malin et al. |
| 6,045,509 A | 4/2000 | Caro et al. |
| 6,061,584 A | 5/2000 | Lovejoy et al. |
| 6,066,204 A | 5/2000 | Haven |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,115,673 A | 9/2000 | Malin et al. |
| 6,124,597 A | 9/2000 | Shehada et al. |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,255,708 B1 | 7/2001 | Sudharsanan et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,280,381 B1 | 8/2001 | Malin et al. |
| 6,285,896 B1 | 9/2001 | Tobler et al. |
| 6,301,493 B1 | 10/2001 | Marro et al. |
| 6,308,089 B1 | 10/2001 | von der Ruhr et al. |
| 6,317,627 B1 | 11/2001 | Ennen et al. |
| 6,321,000 B1 | 11/2001 | King |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,381,489 B1 | 4/2002 | Ashibe |
| 6,388,240 B2 | 5/2002 | Schulz et al. |
| 6,397,091 B2 | 5/2002 | Diab et al. |
| 6,411,373 B1 | 6/2002 | Garside et al. |
| 6,415,167 B1 | 7/2002 | Blank et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,487,429 B2 | 11/2002 | Hockersmith et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,484 B1 | 2/2003 | Lovejoy et al. |
| 6,519,487 B1 | 2/2003 | Parker |
| 6,525,386 B1 | 2/2003 | Mills et al. |
| 6,526,300 B1 | 2/2003 | Kiani et al. |
| 6,534,012 B1 | 3/2003 | Hazen et al. |
| 6,541,756 B2 | 4/2003 | Schulz et al. |
| 6,542,764 B1 | 4/2003 | Al-Ali et al. |
| 6,571,113 B1 | 5/2003 | Fein et al. |
| 6,580,086 B1 | 6/2003 | Schulz et al. |
| 6,580,948 B2 | 6/2003 | Haupert et al. |
| 6,584,336 B1 | 6/2003 | Ali et al. |
| 6,587,196 B1 | 7/2003 | Stippick et al. |
| 6,587,199 B1 | 7/2003 | Luu |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,600,940 B1 | 7/2003 | Fein et al. |
| 6,606,511 B1 | 8/2003 | Ali et al. |
| 6,632,181 B2 | 10/2003 | Flaherty et al. |
| 6,635,559 B2 | 10/2003 | Greenwald et al. |
| 6,639,668 B1 | 10/2003 | Trepagnier |
| 6,640,116 B2 | 10/2003 | Diab |
| 6,640,117 B2 | 10/2003 | Makarewicz et al. |
| 6,643,530 B2 | 11/2003 | Diab et al. |
| 6,650,917 B2 | 11/2003 | Diab et al. |
| 6,654,621 B2 | 11/2003 | Palatnik |
| 6,654,624 B2 | 11/2003 | Diab et al. |
| 6,658,276 B2 | 12/2003 | Kiani et al. |
| 6,661,161 B1 | 12/2003 | Lanzo et al. |
| 6,671,531 B2 | 12/2003 | Al-Ali |
| 6,671,532 B1 | 12/2003 | Fudge et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,738,652 B2 | 5/2004 | Mattu et al. |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,788,965 B2 | 9/2004 | Ruchti et al. |
| 6,792,300 B1 | 9/2004 | Diab et al. |
| 6,813,511 B2 | 11/2004 | Diab et al. |
| 6,816,241 B2 | 11/2004 | Grubisic |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,839,583 B1 | 1/2005 | Lewandowski et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,876,931 B2 | 4/2005 | Lorenz et al. |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,941,162 B2 | 9/2005 | Fudge et al. |
| 6,943,348 B1 | 9/2005 | Coffin IV |
| 6,950,687 B2 | 9/2005 | Al-Ali |
| 6,956,649 B2 | 10/2005 | Acosta et al. |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,990,364 B2 | 1/2006 | Ruchti et al. |
| 6,993,371 B2 | 1/2006 | Kiani et al. |
| 6,996,427 B2 | 2/2006 | Ali et al. |
| 6,998,247 B2 | 2/2006 | Monfre et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,048,687 B1 | 5/2006 | Reuss et al. |

(56) References Cited

U.S. PATENT DOCUMENTS

| | | |
|---|---|---|
| 7,067,893 B2 | 6/2006 | Mills et al. |
| D526,719 S | 8/2006 | Richie, Jr. et al. |
| 7,096,052 B2 | 8/2006 | Mason et al. |
| 7,096,054 B2 | 8/2006 | Abdul-Hafiz et al. |
| D529,616 S | 10/2006 | Deros et al. |
| 7,132,641 B2 | 11/2006 | Schulz et al. |
| 7,133,710 B2 | 11/2006 | Acosta et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab et al. |
| 7,215,986 B2 | 5/2007 | Diab et al. |
| 7,221,971 B2 | 5/2007 | Diab et al. |
| 7,225,006 B2 | 5/2007 | Al-Ali et al. |
| 7,225,007 B2 | 5/2007 | Al-Ali et al. |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali et al. |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali et al. |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,383,070 B2 | 6/2008 | Diab et al. |
| 7,395,158 B2 | 7/2008 | Monfre et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,739 B2 | 3/2009 | Sweitzer |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,514,725 B2 | 4/2009 | Wojtczuk et al. |
| 7,519,406 B2 | 4/2009 | Blank et al. |
| 7,526,328 B2 | 4/2009 | Diab et al. |
| D592,507 S | 5/2009 | Wachman et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,593,230 B2 | 9/2009 | Abul-Haj et al. |
| 7,596,398 B2 | 9/2009 | Al-Ali et al. |
| 7,606,608 B2 | 10/2009 | Blank et al. |
| 7,618,375 B2 | 11/2009 | Flaherty et al. |
| 7,620,674 B2 | 11/2009 | Ruchti et al. |
| D606,659 S | 12/2009 | Kiani et al. |
| 7,629,039 B2 | 12/2009 | Eckerbom et al. |
| 7,640,140 B2 | 12/2009 | Ruchti et al. |
| 7,647,083 B2 | 1/2010 | Al-Ali et al. |
| D609,193 S | 2/2010 | Al-Ali et al. |
| D614,305 S | 4/2010 | Al-Ali et al. |
| 7,697,966 B2 | 4/2010 | Monfre et al. |
| 7,698,105 B2 | 4/2010 | Ruchti et al. |
| 7,706,853 B2 | 4/2010 | Hacker et al. |
| RE41,317 E | 5/2010 | Parker |
| RE41,333 E | 5/2010 | Blank et al. |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |

(56) References Cited

U.S. PATENT DOCUMENTS

| | | |
|---|---|---|
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,532 B2 | 7/2012 | Davis |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,280,473 B2 | 10/2012 | Al-Ali |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-Ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellott et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,581,732 B2 | 11/2013 | Al-Ali et al. |
| 8,584,345 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,688,183 B2 | 4/2014 | Bruinsma et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |

(56) References Cited

U.S. PATENT DOCUMENTS

| | | |
|---|---|---|
| 9,028,429 B2 | 5/2015 | Telfort et al. |
| 9,037,207 B2 | 5/2015 | Al-Ali et al. |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,176,141 B2 | 11/2015 | Al-Ali et al. |
| 9,186,102 B2 | 11/2015 | Bruinsma et al. |
| 9,192,312 B2 | 11/2015 | Al-Ali |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,072 B2 | 12/2015 | Kiani |
| 9,211,095 B1 | 12/2015 | Al-Ali |
| 9,218,454 B2 | 12/2015 | Kiani et al. |
| 9,226,696 B2 | 1/2016 | Kiani |
| 9,241,662 B2 | 1/2016 | Al-Ali et al. |
| 9,245,668 B1 | 1/2016 | Vo et al. |
| 9,259,185 B2 | 2/2016 | Abdul-Hafiz et al. |
| 9,267,572 B2 | 2/2016 | Barker et al. |
| 9,277,880 B2 | 3/2016 | Poeze et al. |
| 9,289,167 B2 | 3/2016 | Diab et al. |
| 9,295,421 B2 | 3/2016 | Kiani et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,333,316 B2 | 5/2016 | Kiani |
| 9,339,220 B2 | 5/2016 | Lamego et al. |
| 9,341,565 B2 | 5/2016 | Lamego et al. |
| 9,351,673 B2 | 5/2016 | Diab et al. |
| 9,351,675 B2 | 5/2016 | Al-Ali et al. |
| 9,364,181 B2 | 6/2016 | Kiani et al. |
| 9,368,671 B2 | 6/2016 | Wojtczuk et al. |
| 9,370,325 B2 | 6/2016 | Al-Ali et al. |
| 9,370,326 B2 | 6/2016 | McHale et al. |
| 9,370,335 B2 | 6/2016 | Al-Ali et al. |
| 9,375,185 B2 | 6/2016 | Ali et al. |
| 9,386,953 B2 | 7/2016 | Al-Ali |
| 9,386,961 B2 | 7/2016 | Al-Ali et al. |
| 9,392,945 B2 | 7/2016 | Al-Ali et al. |
| 9,397,448 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,466,919 B2 | 10/2016 | Kiani et al. |
| 9,474,474 B2 | 10/2016 | Lamego et al. |
| 9,480,422 B2 | 11/2016 | Al-Ali |
| 9,480,435 B2 | 11/2016 | Olsen |
| 9,492,110 B2 | 11/2016 | Al-Ali et al. |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,538,949 B2 | 1/2017 | Al-Ali et al. |
| 9,538,980 B2 | 1/2017 | Telfort et al. |
| 9,549,696 B2 | 1/2017 | Lamego et al. |
| 9,554,737 B2 | 1/2017 | Schurman et al. |
| 9,560,996 B2 | 2/2017 | Kiani |
| 9,560,998 B2 | 2/2017 | Al-Ali et al. |
| 9,566,019 B2 | 2/2017 | Al-Ali et al. |
| 9,579,039 B2 | 2/2017 | Jansen et al. |
| 9,591,975 B2 | 3/2017 | Dalvi et al. |
| 9,622,692 B2 | 4/2017 | Lamego et al. |
| 9,622,693 B2 | 4/2017 | Diab |
| D788,312 S | 5/2017 | Al-Ali et al. |
| 9,636,055 B2 | 5/2017 | Al Ali et al. |
| 9,636,056 B2 | 5/2017 | Al-Ali |
| 9,649,054 B2 | 5/2017 | Lamego et al. |
| 9,662,052 B2 | 5/2017 | Al-Ali et al. |
| 9,668,679 B2 | 6/2017 | Schurman et al. |
| 9,668,680 B2 | 6/2017 | Bruinsma et al. |
| 9,668,703 B2 | 6/2017 | Al-Ali |
| 9,675,286 B2 | 6/2017 | Diab |
| 9,687,160 B2 | 6/2017 | Kiani |
| 9,693,719 B2 | 7/2017 | Al-Ali et al. |
| 9,693,737 B2 | 7/2017 | Al-Ali |
| 9,697,928 B2 | 7/2017 | Al-Ali et al. |
| 9,717,425 B2 | 8/2017 | Kiani et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,730,640 B2 | 8/2017 | Diab et al. |
| 9,743,887 B2 | 8/2017 | Al-Ali et al. |
| 9,749,232 B2 | 8/2017 | Sampath et al. |
| 9,750,442 B2 | 9/2017 | Olsen |
| 9,750,443 B2 | 9/2017 | Smith et al. |
| 9,750,461 B1 | 9/2017 | Telfort |
| 9,775,545 B2 | 10/2017 | Al-Ali et al. |
| 9,775,546 B2 | 10/2017 | Diab et al. |
| 9,775,570 B2 | 10/2017 | Al-Ali |
| 9,778,079 B1 | 10/2017 | Al-Ali et al. |
| 9,782,077 B2 | 10/2017 | Lamego et al. |
| 9,782,110 B2 | 10/2017 | Kiani |
| 9,787,568 B2 | 10/2017 | Lamego et al. |
| 9,788,735 B2 | 10/2017 | Al-Ali |
| 9,788,768 B2 | 10/2017 | Al-Ali et al. |
| 9,795,300 B2 | 10/2017 | Al-Ali |
| 9,795,310 B2 | 10/2017 | Al-Ali |
| 9,795,358 B2 | 10/2017 | Telfort et al. |
| 9,795,739 B2 | 10/2017 | Al-Ali et al. |
| 9,801,556 B2 | 10/2017 | Kiani |
| 9,801,588 B2 | 10/2017 | Weber et al. |
| 9,808,188 B1 | 11/2017 | Perea et al. |
| 9,814,418 B2 | 11/2017 | Weber et al. |
| 9,820,691 B2 | 11/2017 | Kiani |
| 9,833,152 B2 | 12/2017 | Kiani et al. |
| 9,833,180 B2 | 12/2017 | Shakespeare et al. |
| 9,839,379 B2 | 12/2017 | Al-Ali et al. |
| 9,839,381 B1 | 12/2017 | Weber et al. |
| 9,847,002 B2 | 12/2017 | Kiani et al. |
| 9,847,749 B2 | 12/2017 | Kiani et al. |
| 9,848,800 B1 | 12/2017 | Lee et al. |
| 9,848,806 B2 | 12/2017 | Al-Ali |
| 9,848,807 B2 | 12/2017 | Lamego |
| 9,861,298 B2 | 1/2018 | Eckerbom et al. |
| 9,861,304 B2 | 1/2018 | Al-Ali et al. |
| 9,861,305 B1 | 1/2018 | Weber et al. |
| 9,867,578 B2 | 1/2018 | Al-Ali et al. |
| 9,872,623 B2 | 1/2018 | Al-Ali |
| 9,876,320 B2 | 1/2018 | Coverston et al. |
| 9,877,650 B2 | 1/2018 | Muhsin et al. |
| 9,877,686 B2 | 1/2018 | Al-Ali et al. |
| 9,891,079 B2 | 2/2018 | Dalvi |
| 9,895,107 B2 | 2/2018 | Al-Ali et al. |
| 9,913,617 B2 | 3/2018 | Al-Ali et al. |
| 9,924,893 B2 | 3/2018 | Schurman et al. |
| 9,924,897 B1 | 3/2018 | Abdul-Hafiz |
| 9,936,917 B2 | 4/2018 | Poeze et al. |
| 9,943,269 B2 | 4/2018 | Muhsin et al. |
| 9,949,676 B2 | 4/2018 | Al-Ali |
| 9,955,937 B2 | 5/2018 | Telfort |

(56) References Cited

U.S. PATENT DOCUMENTS

| | | |
|---|---|---|
| 9,965,946 B2 | 5/2018 | Al-Ali et al. |
| 9,980,667 B2 | 5/2018 | Kiani et al. |
| D820,865 S | 6/2018 | Muhsin et al. |
| 9,986,919 B2 | 6/2018 | Lamego et al. |
| 9,986,952 B2 | 6/2018 | Dalvi et al. |
| 9,989,560 B2 | 6/2018 | Poeze et al. |
| 9,993,207 B2 | 6/2018 | Al-Ali et al. |
| 10,007,758 B2 | 6/2018 | Al-Ali et al. |
| D822,215 S | 7/2018 | Al-Ali et al. |
| D822,216 S | 7/2018 | Barker et al. |
| 10,010,276 B2 | 7/2018 | Al-Ali et al. |
| 10,032,002 B2 | 7/2018 | Kiani et al. |
| 10,039,482 B2 | 8/2018 | Al-Ali et al. |
| 10,052,037 B2 | 8/2018 | Kinast et al. |
| 10,058,275 B2 | 8/2018 | Al-Ali et al. |
| 10,064,562 B2 | 9/2018 | Al-Ali |
| 10,086,138 B1 | 10/2018 | Novak, Jr. |
| 10,092,200 B2 | 10/2018 | Al-Ali et al. |
| 10,092,249 B2 | 10/2018 | Kiani et al. |
| 10,098,550 B2 | 10/2018 | Al-Ali et al. |
| 10,098,591 B2 | 10/2018 | Al-Ali et al. |
| 10,098,610 B2 | 10/2018 | Al-Ali et al. |
| 10,111,591 B2 | 10/2018 | Dyell et al. |
| D833,624 S | 11/2018 | DeJong et al. |
| 10,123,726 B2 | 11/2018 | Al-Ali et al. |
| 10,123,729 B2 | 11/2018 | Dyell et al. |
| 10,130,289 B2 | 11/2018 | Al-Ali et al. |
| 10,130,291 B2 | 11/2018 | Schurman et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,188,296 B2 | 1/2019 | Al-Ali et al. |
| 10,188,331 B1 | 1/2019 | Kiani et al. |
| 10,188,348 B2 | 1/2019 | Al-Ali et al. |
| RE47,218 E | 2/2019 | Al-Ali |
| RE47,244 E | 2/2019 | Kiani et al. |
| RE47,249 E | 2/2019 | Kiani et al. |
| 10,194,847 B2 | 2/2019 | Al-Ali |
| 10,194,848 B1 | 2/2019 | Kiani et al. |
| 10,201,298 B2 | 2/2019 | Al-Ali et al. |
| 10,205,272 B2 | 2/2019 | Kiani et al. |
| 10,205,291 B2 | 2/2019 | Scruggs et al. |
| 10,213,108 B2 | 2/2019 | Al-Ali |
| 10,219,706 B2 | 3/2019 | Al-Ali |
| 10,219,746 B2 | 3/2019 | McHale et al. |
| 10,226,187 B2 | 3/2019 | Al-Ali et al. |
| 10,226,576 B2 | 3/2019 | Kiani |
| 10,231,657 B2 | 3/2019 | Al-Ali et al. |
| 10,231,670 B2 | 3/2019 | Blank et al. |
| 10,231,676 B2 | 3/2019 | Al-Ali et al. |
| RE47,353 E | 4/2019 | Kiani et al. |
| 10,251,585 B2 | 4/2019 | Al-Ali et al. |
| 10,251,586 B2 | 4/2019 | Lamego |
| 10,255,994 B2 | 4/2019 | Sampath et al. |
| 10,258,265 B1 | 4/2019 | Poeze et al. |
| 10,258,266 B1 | 4/2019 | Poeze et al. |
| 10,271,748 B2 | 4/2019 | Al-Ali |
| 10,279,247 B2 | 5/2019 | Kiani |
| 10,292,664 B2 | 5/2019 | Al-Ali |
| 10,299,720 B2 | 5/2019 | Brown et al. |
| 10,327,337 B2 | 6/2019 | Schmidt et al. |
| 10,327,713 B2 | 6/2019 | Barker et al. |
| 10,332,630 B2 | 6/2019 | Al-Ali |
| 10,383,520 B2 | 8/2019 | Wojtczuk et al. |
| 10,383,527 B2 | 8/2019 | Al-Ali |
| 10,388,120 B2 | 8/2019 | Muhsin et al. |
| D864,120 S | 10/2019 | Forrest et al. |
| 10,441,181 B1 | 10/2019 | Telfort et al. |
| 10,441,196 B2 | 10/2019 | Eckerbom et al. |
| 10,448,844 B2 | 10/2019 | Al-Ali et al. |
| 10,448,871 B2 | 10/2019 | Al-Ali et al. |
| 10,456,038 B2 | 10/2019 | Lamego et al. |
| 10,463,340 B2 | 11/2019 | Telfort et al. |
| 10,471,159 B1 | 11/2019 | Lapotko et al. |
| 10,505,311 B2 | 12/2019 | Al-Ali et al. |
| 10,524,738 B2 | 1/2020 | Olsen |
| 10,532,174 B2 | 1/2020 | Al-Ali |
| 10,537,285 B2 | 1/2020 | Shreim et al. |
| 10,542,903 B2 | 1/2020 | Al-Ali et al. |
| 10,555,678 B2 | 2/2020 | Dalvi et al. |
| 10,568,553 B2 | 2/2020 | O'Neil et al. |
| RE47,882 E | 3/2020 | Al-Ali |
| 10,608,817 B2 | 3/2020 | Haider et al. |
| D880,477 S | 4/2020 | Forrest et al. |
| 10,617,302 B2 | 4/2020 | Al-Ali et al. |
| 10,617,335 B2 | 4/2020 | Al-Ali et al. |
| 10,637,181 B2 | 4/2020 | Al-Ali et al. |
| D886,849 S | 6/2020 | Muhsin et al. |
| D887,548 S | 6/2020 | Abdul-Hafiz et al. |
| D887,549 S | 6/2020 | Abdul-Hafiz et al. |
| 10,667,764 B2 | 6/2020 | Ahmed et al. |
| D890,708 S | 7/2020 | Forrest et al. |
| 10,721,785 B2 | 7/2020 | Al-Ali |
| 10,736,518 B2 | 8/2020 | Al-Ali et al. |
| 10,750,984 B2 | 8/2020 | Pauley et al. |
| D897,098 S | 9/2020 | Al-Ali |
| 10,779,098 B2 | 9/2020 | Iswanto et al. |
| 10,827,961 B1 | 11/2020 | Iyengar et al. |
| 10,828,007 B1 | 11/2020 | Telfort et al. |
| 10,832,818 B2 | 11/2020 | Muhsin et al. |
| 10,849,554 B2 | 12/2020 | Shreim et al. |
| 10,856,750 B2 | 12/2020 | Indorf |
| D906,970 S | 1/2021 | Forrest et al. |
| D908,213 S | 1/2021 | Abdul-Hafiz et al. |
| 10,918,281 B2 | 2/2021 | Al-Ali et al. |
| 10,932,705 B2 | 3/2021 | Muhsin et al. |
| 10,932,729 B2 | 3/2021 | Kiani et al. |
| 10,939,878 B2 | 3/2021 | Kiani et al. |
| 10,956,950 B2 | 3/2021 | Al-Ali et al. |
| D916,135 S | 4/2021 | Indorf et al. |
| D917,046 S | 4/2021 | Abdul-Hafiz et al. |
| D917,550 S | 4/2021 | Indorf et al. |
| D917,564 S | 4/2021 | Indorf et al. |
| D917,704 S | 4/2021 | Al-Ali et al. |
| 10,987,066 B2 | 4/2021 | Chandran et al. |
| 10,991,135 B2 | 4/2021 | Al-Ali et al. |
| D919,094 S | 5/2021 | Al-Ali et al. |
| D919,100 S | 5/2021 | Al-Ali et al. |
| 11,006,867 B2 | 5/2021 | Al-Ali |
| D921,202 S | 6/2021 | Al-Ali et al. |
| 11,024,064 B2 | 6/2021 | Muhsin et al. |
| 11,026,604 B2 | 6/2021 | Chen et al. |
| D925,597 S | 7/2021 | Chandran et al. |
| D927,699 S | 8/2021 | Al-Ali et al. |
| 11,076,777 B2 | 8/2021 | Lee et al. |
| 11,114,188 B2 | 9/2021 | Poeze et al. |
| D933,232 S | 10/2021 | Al-Ali et al. |
| D933,233 S | 10/2021 | Al-Ali et al. |
| D933,234 S | 10/2021 | Al-Ali et al. |
| 11,145,408 B2 | 10/2021 | Sampath et al. |
| 11,147,518 B1 | 10/2021 | Al-Ali et al. |
| 11,185,262 B2 | 11/2021 | Al-Ali et al. |
| 11,191,484 B2 | 12/2021 | Kiani et al. |
| D946,596 S | 3/2022 | Ahmed |
| D946,597 S | 3/2022 | Ahmed |
| D946,598 S | 3/2022 | Ahmed |
| D946,617 S | 3/2022 | Ahmed |
| 11,272,839 B2 | 3/2022 | Al-Ali et al. |
| 11,289,199 B2 | 3/2022 | Al-Ali |
| RE49,034 E | 4/2022 | Al-Ali |
| 11,298,021 B2 | 4/2022 | Muhsin et al. |
| D950,580 S | 5/2022 | Ahmed |
| D950,599 S | 5/2022 | Ahmed |
| D950,738 S | 5/2022 | Al-Ali et al. |
| 11,331,042 B2 | 5/2022 | Al-Ali et al. |
| D957,648 S | 7/2022 | Al-Ali |
| 11,382,567 B2 | 7/2022 | O'Brien et al. |
| 11,389,093 B2 | 7/2022 | Triman et al. |
| 11,406,286 B2 | 8/2022 | Al-Ali et al. |
| 11,417,426 B2 | 8/2022 | Muhsin et al. |

(56) References Cited

U.S. PATENT DOCUMENTS

| | | |
|---|---|---|
| 11,439,329 B2 | 9/2022 | Lamego |
| 11,445,948 B2 | 9/2022 | Scruggs et al. |
| D965,789 S | 10/2022 | Al-Ali et al. |
| D967,433 S | 10/2022 | Al-Ali et al. |
| 11,464,410 B2 | 10/2022 | Muhsin |
| 11,504,058 B1 | 11/2022 | Sharma et al. |
| 11,504,066 B1 | 11/2022 | Dalvi et al. |
| D971,933 S | 12/2022 | Ahmed |
| D973,072 S | 12/2022 | Ahmed |
| D973,685 S | 12/2022 | Ahmed |
| D973,686 S | 12/2022 | Ahmed |
| D974,193 S | 1/2023 | Forrest et al. |
| D979,516 S | 2/2023 | Al-Ali et al. |
| D980,091 S | 3/2023 | Forrest et al. |
| 11,596,363 B2 | 3/2023 | Lamego |
| 11,627,919 B2 | 4/2023 | Kiani et al. |
| 11,637,437 B2 | 4/2023 | Al-Ali et al. |
| D985,498 S | 5/2023 | Al-Ali et al. |
| 11,653,862 B2 | 5/2023 | Dalvi et al. |
| D989,112 S | 6/2023 | Muhsin et al. |
| D989,327 S | 6/2023 | Al-Ali et al. |
| 11,678,829 B2 | 6/2023 | Al-Ali et al. |
| 11,679,579 B2 | 6/2023 | Al-Ali |
| 11,684,296 B2 | 6/2023 | Vo et al. |
| 11,692,934 B2 | 7/2023 | Normand et al. |
| 11,701,043 B2 | 7/2023 | Al-Ali et al. |
| D997,365 S | 8/2023 | Hwang |
| 11,721,105 B2 | 8/2023 | Ranasinghe et al. |
| 11,730,379 B2 | 8/2023 | Ahmed et al. |
| D998,625 S | 9/2023 | Indorf et al. |
| D998,630 S | 9/2023 | Indorf et al. |
| D998,631 S | 9/2023 | Indorf et al. |
| D999,244 S | 9/2023 | Indorf et al. |
| D999,245 S | 9/2023 | Indorf et al. |
| D999,246 S | 9/2023 | Indorf et al. |
| 11,766,198 B2 | 9/2023 | Pauley et al. |
| D1,000,975 S | 10/2023 | Al-Ali et al. |
| 11,803,623 B2 | 10/2023 | Kiani et al. |
| 11,832,940 B2 | 12/2023 | Diab et al. |
| D1,013,179 S | 1/2024 | Al-Ali et al. |
| 11,872,156 B2 | 1/2024 | Telfort et al. |
| 11,879,960 B2 | 1/2024 | Ranasinghe et al. |
| 11,883,129 B2 | 1/2024 | Olsen |
| D1,022,729 S | 4/2024 | Forrest et al. |
| 11,951,186 B2 | 4/2024 | Krishnamani et al. |
| 11,974,833 B2 | 5/2024 | Forrest et al. |
| 11,986,067 B2 | 5/2024 | Al-Ali et al. |
| 11,986,289 B2 | 5/2024 | Dalvi et al. |
| 11,986,305 B2 | 5/2024 | Al-Ali et al. |
| D1,031,729 S | 6/2024 | Forrest et al. |
| 12,004,869 B2 | 6/2024 | Kiani et al. |
| 12,014,328 B2 | 6/2024 | Wachman et al. |
| D1,036,293 S | 7/2024 | Al-Ali et al. |
| D1,037,462 S | 7/2024 | Al-Ali et al. |
| 12,029,844 B2 | 7/2024 | Pauley et al. |
| 12,048,534 B2 | 7/2024 | Vo et al. |
| 12,064,217 B2 | 8/2024 | Ahmed et al. |
| 12,066,426 B1 | 8/2024 | Lapotko et al. |
| D1,041,511 S | 9/2024 | Indorf et al. |
| D1,042,596 S | 9/2024 | DeJong et al. |
| D1,042,852 S | 9/2024 | Hwang |
| 12,076,159 B2 | 9/2024 | Belur Nagaraj et al. |
| 12,082,926 B2 | 9/2024 | Sharma et al. |
| D1,044,828 S | 10/2024 | Chandran et al. |
| D1,048,571 S | 10/2024 | Yu et al. |
| D1,048,908 S | 10/2024 | Al-Ali et al. |
| 12,106,752 B2 | 10/2024 | Campbell et al. |
| 12,114,974 B2 | 10/2024 | Al-Ali et al. |
| 12,126,683 B2 | 10/2024 | Koo et al. |
| 12,127,838 B2 | 10/2024 | Olsen et al. |
| 12,128,213 B2 | 10/2024 | Kiani et al. |
| 12,131,661 B2 | 10/2024 | Pauley et al. |
| D1,050,910 S | 11/2024 | Al-Ali et al. |
| 2001/0034477 A1 | 10/2001 | Mansfield et al. |
| 2001/0039483 A1 | 11/2001 | Brand et al. |
| 2002/0010401 A1 | 1/2002 | Bushmakin et al. |
| 2002/0058864 A1 | 5/2002 | Mansfield et al. |
| 2002/0133080 A1 | 9/2002 | Apruzzese et al. |
| 2003/0013975 A1 | 1/2003 | Kiani |
| 2003/0018243 A1 | 1/2003 | Gerhardt et al. |
| 2003/0144582 A1 | 7/2003 | Cohen et al. |
| 2003/0156288 A1 | 8/2003 | Barnum et al. |
| 2003/0212312 A1 | 11/2003 | Coffin, IV et al. |
| 2004/0106163 A1 | 6/2004 | Workman, Jr. et al. |
| 2005/0055276 A1 | 3/2005 | Kiani et al. |
| 2005/0075550 A1 | 4/2005 | Lindelkugel |
| 2005/0234317 A1 | 10/2005 | Kiani |
| 2006/0015023 A1 | 1/2006 | Monfre et al. |
| 2006/0053522 A1 | 3/2006 | Kimbell |
| 2006/0073719 A1 | 4/2006 | Kiani |
| 2006/0161054 A1 | 7/2006 | Reuss et al. |
| 2006/0189871 A1 | 8/2006 | Al-Ali et al. |
| 2007/0073116 A1 | 3/2007 | Kiani et al. |
| 2007/0100219 A1 | 5/2007 | Sweitzer |
| 2007/0180140 A1 | 8/2007 | Welch et al. |
| 2007/0244377 A1 | 10/2007 | Cozad et al. |
| 2008/0064965 A1 | 3/2008 | Jay et al. |
| 2008/0076982 A1 | 3/2008 | Ollerdessen et al. |
| 2008/0088467 A1 | 4/2008 | Al-Ali |
| 2008/0094228 A1 | 4/2008 | Welch et al. |
| 2008/0103375 A1 | 5/2008 | Kiani |
| 2008/0221418 A1 | 9/2008 | Al-Ali et al. |
| 2008/0262324 A1 | 10/2008 | Van Der Voort et al. |
| 2009/0036759 A1 | 2/2009 | Ault et al. |
| 2009/0093687 A1 | 4/2009 | Telfort et al. |
| 2009/0095926 A1 | 4/2009 | MacNeish, III |
| 2009/0247984 A1 | 10/2009 | Lamego et al. |
| 2009/0275813 A1 | 11/2009 | Davis |
| 2009/0275844 A1 | 11/2009 | Al-Ali |
| 2010/0004518 A1 | 1/2010 | Vo et al. |
| 2010/0030040 A1 | 2/2010 | Poeze et al. |
| 2010/0099964 A1 | 4/2010 | O'Reilly et al. |
| 2010/0234718 A1 | 9/2010 | Sampath et al. |
| 2010/0240972 A1 | 9/2010 | Neal |
| 2010/0270257 A1 | 10/2010 | Wachman et al. |
| 2010/0305417 A1 | 12/2010 | Kumazaki |
| 2011/0028806 A1 | 2/2011 | Merritt et al. |
| 2011/0028809 A1 | 2/2011 | Goodman |
| 2011/0038754 A1 | 2/2011 | James |
| 2011/0040197 A1 | 2/2011 | Welch et al. |
| 2011/0082711 A1 | 4/2011 | Poeze et al. |
| 2011/0087081 A1 | 4/2011 | Kiani et al. |
| 2011/0118561 A1 | 5/2011 | Tari et al. |
| 2011/0125060 A1 | 5/2011 | Telfort et al. |
| 2011/0137297 A1 | 6/2011 | Kiani et al. |
| 2011/0172498 A1 | 7/2011 | Olsen et al. |
| 2011/0208015 A1 | 8/2011 | Welch et al. |
| 2011/0230733 A1 | 9/2011 | Al-Ali |
| 2011/0261528 A1 | 10/2011 | Gandhi |
| 2012/0123231 A1 | 5/2012 | O'Reilly |
| 2012/0165629 A1 | 6/2012 | Merritt et al. |
| 2012/0202361 A1 | 8/2012 | Terhune |
| 2012/0209082 A1 | 8/2012 | Al-Ali |
| 2012/0209084 A1 | 8/2012 | Olsen et al. |
| 2012/0226117 A1 | 9/2012 | Lamego et al. |
| 2012/0283524 A1 | 11/2012 | Kiani et al. |
| 2013/0023775 A1 | 1/2013 | Lamego et al. |
| 2013/0041591 A1 | 2/2013 | Lamego |
| 2013/0060147 A1 | 3/2013 | Welch et al. |
| 2013/0096405 A1 | 4/2013 | Garfio |
| 2013/0096936 A1 | 4/2013 | Sampath et al. |
| 2013/0243021 A1 | 9/2013 | Siskavich |
| 2013/0296672 A1 | 11/2013 | O'Neil et al. |
| 2013/0324808 A1 | 12/2013 | Al-Ali et al. |
| 2013/0331660 A1 | 12/2013 | Al-Ali et al. |
| 2013/0345921 A1 | 12/2013 | Al-Ali et al. |
| 2014/0012100 A1 | 1/2014 | Al-Ali et al. |
| 2014/0051953 A1 | 2/2014 | Lamego et al. |
| 2014/0120564 A1 | 5/2014 | Workman et al. |
| 2014/0121482 A1 | 5/2014 | Merritt et al. |
| 2014/0127137 A1 | 5/2014 | Bellott et al. |
| 2014/0163344 A1 | 6/2014 | Al-Ali |
| 2014/0166076 A1 | 6/2014 | Kiani et al. |
| 2014/0171763 A1 | 6/2014 | Diab |

(56) References Cited

U.S. PATENT DOCUMENTS

| | | |
|---|---|---|
| 2014/0180154 A1 | 6/2014 | Sierra et al. |
| 2014/0180160 A1 | 6/2014 | Brown et al. |
| 2014/0187973 A1 | 7/2014 | Brown et al. |
| 2014/0213864 A1 | 7/2014 | Abdul-Hafiz et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0288400 A1 | 9/2014 | Diab et al. |
| 2014/0316217 A1 | 10/2014 | Purdon et al. |
| 2014/0316218 A1 | 10/2014 | Purdon et al. |
| 2014/0316228 A1 | 10/2014 | Blank et al. |
| 2014/0323825 A1 | 10/2014 | Al-Ali et al. |
| 2014/0323897 A1 | 10/2014 | Brown et al. |
| 2014/0323898 A1 | 10/2014 | Purdon et al. |
| 2014/0330098 A1 | 11/2014 | Merritt et al. |
| 2014/0357966 A1 | 12/2014 | Al-Ali et al. |
| 2015/0005600 A1 | 1/2015 | Blank et al. |
| 2015/0011907 A1 | 1/2015 | Purdon et al. |
| 2015/0032029 A1 | 1/2015 | Al-Ali et al. |
| 2015/0038859 A1 | 2/2015 | Dalvi et al. |
| 2015/0073241 A1 | 3/2015 | Lamego |
| 2015/0080754 A1 | 3/2015 | Purdon et al. |
| 2015/0087936 A1 | 3/2015 | Al-Ali et al. |
| 2015/0094546 A1 | 4/2015 | Al-Ali |
| 2015/0099950 A1 | 4/2015 | Al-Ali et al. |
| 2015/0101844 A1 | 4/2015 | Al-Ali et al. |
| 2015/0106121 A1 | 4/2015 | Muhsin et al. |
| 2015/0112151 A1 | 4/2015 | Muhsin et al. |
| 2015/0196249 A1 | 7/2015 | Brown et al. |
| 2015/0216459 A1 | 8/2015 | Al-Ali et al. |
| 2015/0238722 A1 | 8/2015 | Al-Ali |
| 2015/0257689 A1 | 9/2015 | Al-Ali et al. |
| 2015/0351697 A1 | 12/2015 | Weber et al. |
| 2015/0366507 A1 | 12/2015 | Blank et al. |
| 2016/0029932 A1 | 2/2016 | Al-Ali |
| 2016/0058347 A1 | 3/2016 | Reichgott et al. |
| 2016/0066824 A1 | 3/2016 | Al-Ali et al. |
| 2016/0081552 A1 | 3/2016 | Wojtczuk et al. |
| 2016/0095543 A1 | 4/2016 | Telfort et al. |
| 2016/0103598 A1 | 4/2016 | Al-Ali et al. |
| 2016/0166183 A1 | 6/2016 | Poeze et al. |
| 2016/0196388 A1 | 7/2016 | Lamego |
| 2016/0197436 A1 | 7/2016 | Barker et al. |
| 2016/0213281 A1 | 7/2016 | Eckerbom et al. |
| 2016/0228043 A1 | 8/2016 | O'Neil et al. |
| 2016/0234944 A1 | 8/2016 | Schmidt et al. |
| 2016/0270735 A1 | 9/2016 | Diab et al. |
| 2016/0283665 A1 | 9/2016 | Sampath et al. |
| 2016/0287786 A1 | 10/2016 | Kiani |
| 2016/0314260 A1 | 10/2016 | Kiani |
| 2016/0324488 A1 | 11/2016 | Olsen |
| 2016/0327984 A1 | 11/2016 | Al-Ali et al. |
| 2016/0331332 A1 | 11/2016 | Al-Ali |
| 2016/0367173 A1 | 12/2016 | Dalvi et al. |
| 2017/0000394 A1 | 1/2017 | Al-Ali et al. |
| 2017/0007134 A1 | 1/2017 | Al-Ali et al. |
| 2017/0014083 A1 | 1/2017 | Diab et al. |
| 2017/0014084 A1 | 1/2017 | Al-Ali et al. |
| 2017/0024748 A1 | 1/2017 | Haider |
| 2017/0042488 A1 | 2/2017 | Muhsin |
| 2017/0055882 A1 | 3/2017 | Al-Ali et al. |
| 2017/0055887 A1 | 3/2017 | Al-Ali |
| 2017/0055896 A1 | 3/2017 | Al-Ali |
| 2017/0079594 A1 | 3/2017 | Telfort et al. |
| 2017/0086723 A1 | 3/2017 | Al-Ali et al. |
| 2017/0143281 A1 | 5/2017 | Olsen |
| 2017/0147774 A1 | 5/2017 | Kiani |
| 2017/0156620 A1 | 6/2017 | Al-Ali et al. |
| 2017/0173632 A1 | 6/2017 | Al-Ali |
| 2017/0188919 A1 | 7/2017 | Al-Ali et al. |
| 2017/0196464 A1 | 7/2017 | Jansen et al. |
| 2017/0196470 A1 | 7/2017 | Lamego et al. |
| 2017/0228516 A1 | 8/2017 | Sampath et al. |
| 2017/0245790 A1 | 8/2017 | Al-Ali et al. |
| 2017/0251974 A1 | 9/2017 | Shreim et al. |
| 2017/0251975 A1 | 9/2017 | Shreim et al. |
| 2017/0258403 A1 | 9/2017 | Abdul-Hafiz et al. |
| 2017/0311891 A1 | 11/2017 | Kiani et al. |
| 2017/0332976 A1 | 11/2017 | Al-Ali |
| 2017/0340293 A1 | 11/2017 | Al-Ali et al. |
| 2017/0360310 A1 | 12/2017 | Kiani |
| 2018/0008146 A1 | 1/2018 | Al-Ali et al. |
| 2018/0013562 A1 | 1/2018 | Haider et al. |
| 2018/0014752 A1 | 1/2018 | Al-Ali et al. |
| 2018/0028124 A1 | 2/2018 | Al-Ali et al. |
| 2018/0055390 A1 | 3/2018 | Kiani et al. |
| 2018/0055430 A1 | 3/2018 | Diab et al. |
| 2018/0064381 A1 | 3/2018 | Shakespeare et al. |
| 2018/0069776 A1 | 3/2018 | Lamego et al. |
| 2018/0070867 A1 | 3/2018 | Smith et al. |
| 2018/0082767 A1 | 3/2018 | Al-Ali et al. |
| 2018/0085068 A1 | 3/2018 | Telfort |
| 2018/0087937 A1 | 3/2018 | Al-Ali et al. |
| 2018/0103874 A1 | 4/2018 | Lee et al. |
| 2018/0103905 A1 | 4/2018 | Kiani |
| 2018/0110478 A1 | 4/2018 | Al-Ali |
| 2018/0116575 A1 | 5/2018 | Perea et al. |
| 2018/0125368 A1 | 5/2018 | Lamego et al. |
| 2018/0125430 A1 | 5/2018 | Al-Ali et al. |
| 2018/0125445 A1 | 5/2018 | Telfort et al. |
| 2018/0130325 A1 | 5/2018 | Kiani et al. |
| 2018/0132769 A1 | 5/2018 | Weber et al. |
| 2018/0146901 A1 | 5/2018 | Al-Ali et al. |
| 2018/0146902 A1 | 5/2018 | Kiani et al. |
| 2018/0153442 A1 | 6/2018 | Eckerbom et al. |
| 2018/0153446 A1 | 6/2018 | Kiani |
| 2018/0153447 A1 | 6/2018 | Al-Ali et al. |
| 2018/0153448 A1 | 6/2018 | Weber et al. |
| 2018/0161499 A1 | 6/2018 | Al-Ali et al. |
| 2018/0168491 A1 | 6/2018 | Al-Ali et al. |
| 2018/0174679 A1 | 6/2018 | Sampath et al. |
| 2018/0174680 A1 | 6/2018 | Sampath et al. |
| 2018/0184917 A1 | 7/2018 | Kiani |
| 2018/0192924 A1 | 7/2018 | Al-Ali |
| 2018/0192953 A1 | 7/2018 | Shreim et al. |
| 2018/0192955 A1 | 7/2018 | Al-Ali et al. |
| 2018/0199871 A1 | 7/2018 | Pauley et al. |
| 2018/0206795 A1 | 7/2018 | Al-Ali |
| 2018/0206815 A1 | 7/2018 | Telfort |
| 2018/0213583 A1 | 7/2018 | Al-Ali |
| 2018/0214031 A1 | 8/2018 | Kiani et al. |
| 2018/0214090 A1 | 8/2018 | Al-Ali et al. |
| 2018/0218792 A1 | 8/2018 | Muhsin et al. |
| 2018/0225960 A1 | 8/2018 | Al-Ali et al. |
| 2018/0238718 A1 | 8/2018 | Dalvi |
| 2018/0242853 A1 | 8/2018 | Al-Ali |
| 2018/0242921 A1 | 8/2018 | Muhsin et al. |
| 2018/0242923 A1 | 8/2018 | Al-Ali et al. |
| 2018/0242924 A1 | 8/2018 | Barker et al. |
| 2018/0242926 A1 | 8/2018 | Muhsin et al. |
| 2018/0247353 A1 | 8/2018 | Al-Ali et al. |
| 2018/0247712 A1 | 8/2018 | Muhsin et al. |
| 2018/0249933 A1 | 9/2018 | Schurman et al. |
| 2018/0253947 A1 | 9/2018 | Muhsin et al. |
| 2018/0256087 A1 | 9/2018 | Al-Ali et al. |
| 2018/0256113 A1 | 9/2018 | Weber et al. |
| 2018/0285094 A1 | 10/2018 | Housel et al. |
| 2018/0289325 A1 | 10/2018 | Poeze et al. |
| 2018/0289337 A1 | 10/2018 | Al-Ali et al. |
| 2018/0296161 A1 | 10/2018 | Shreim et al. |
| 2018/0300919 A1 | 10/2018 | Muhsin et al. |
| 2018/0310822 A1 | 11/2018 | Indorf et al. |
| 2018/0310823 A1 | 11/2018 | Al-Ali et al. |
| 2018/0317826 A1 | 11/2018 | Muhsin et al. |
| 2018/0317841 A1 | 11/2018 | Novak, Jr. |
| 2018/0333055 A1 | 11/2018 | Lamego et al. |
| 2018/0333087 A1 | 11/2018 | Al-Ali |
| 2019/0000317 A1 | 1/2019 | Muhsin et al. |
| 2019/0000362 A1 | 1/2019 | Kiani et al. |
| 2019/0015023 A1 | 1/2019 | Monfre |
| 2019/0021638 A1 | 1/2019 | Al-Ali et al. |
| 2019/0029574 A1 | 1/2019 | Schurman et al. |
| 2019/0029578 A1 | 1/2019 | Al-Ali et al. |
| 2019/0058280 A1 | 2/2019 | Al-Ali et al. |

(56) References Cited

U.S. PATENT DOCUMENTS

| | | |
|---|---|---|
| 2019/0058281 A1 | 2/2019 | Al-Ali et al. |
| 2019/0069813 A1 | 3/2019 | Al-Ali |
| 2019/0069814 A1 | 3/2019 | Al-Ali |
| 2019/0076028 A1 | 3/2019 | Al-Ali et al. |
| 2019/0082979 A1 | 3/2019 | Al-Ali et al. |
| 2019/0090748 A1 | 3/2019 | Al-Ali |
| 2019/0090760 A1 | 3/2019 | Kinast et al. |
| 2019/0090764 A1 | 3/2019 | Al-Ali |
| 2019/0117070 A1 | 4/2019 | Muhsin et al. |
| 2019/0117139 A1 | 4/2019 | Al-Ali et al. |
| 2019/0117140 A1 | 4/2019 | Al-Ali et al. |
| 2019/0117141 A1 | 4/2019 | Al-Ali |
| 2019/0117930 A1 | 4/2019 | Al-Ali |
| 2019/0122763 A1 | 4/2019 | Sampath et al. |
| 2019/0239787 A1 | 8/2019 | Pauley et al. |
| 2019/0274627 A1 | 9/2019 | Al-Ali et al. |
| 2019/0320906 A1 | 10/2019 | Olsen |
| 2019/0374713 A1 | 12/2019 | Kiani et al. |
| 2020/0060869 A1 | 2/2020 | Telfort et al. |
| 2020/0111552 A1 | 4/2020 | Ahmed |
| 2020/0113435 A1 | 4/2020 | Muhsin |
| 2020/0113488 A1 | 4/2020 | Al-Ali et al. |
| 2020/0113496 A1 | 4/2020 | Scruggs et al. |
| 2020/0113497 A1 | 4/2020 | Triman et al. |
| 2020/0113520 A1 | 4/2020 | Abdul-Hafiz et al. |
| 2020/0138288 A1 | 5/2020 | Al-Ali et al. |
| 2020/0138368 A1 | 5/2020 | Kiani et al. |
| 2020/0163597 A1 | 5/2020 | Dalvi et al. |
| 2020/0196877 A1 | 6/2020 | Vo et al. |
| 2020/0253474 A1 | 8/2020 | Muhsin et al. |
| 2020/0253544 A1 | 8/2020 | Belur Nagaraj et al. |
| 2020/0275841 A1 | 9/2020 | Telfort et al. |
| 2020/0288983 A1 | 9/2020 | Telfort et al. |
| 2020/0321793 A1 | 10/2020 | Al-Ali et al. |
| 2020/0329983 A1 | 10/2020 | Al-Ali et al. |
| 2020/0329984 A1 | 10/2020 | Al-Ali et al. |
| 2020/0329993 A1 | 10/2020 | Al-Ali et al. |
| 2020/0330037 A1 | 10/2020 | Al-Ali et al. |
| 2021/0022628 A1 | 1/2021 | Telfort et al. |
| 2021/0104173 A1 | 4/2021 | Pauley et al. |
| 2021/0113121 A1 | 4/2021 | Diab et al. |
| 2021/0117525 A1 | 4/2021 | Kiani et al. |
| 2021/0118581 A1 | 4/2021 | Kiani et al. |
| 2021/0121582 A1 | 4/2021 | Krishnamani et al. |
| 2021/0161465 A1 | 6/2021 | Barker et al. |
| 2021/0236729 A1 | 8/2021 | Kiani et al. |
| 2021/0256267 A1 | 8/2021 | Ranasinghe et al. |
| 2021/0256835 A1 | 8/2021 | Ranasinghe et al. |
| 2021/0275101 A1 | 9/2021 | Vo et al. |
| 2021/0290060 A1 | 9/2021 | Ahmed |
| 2021/0290072 A1 | 9/2021 | Forrest |
| 2021/0290080 A1 | 9/2021 | Ahmed |
| 2021/0290120 A1 | 9/2021 | Al-Ali |
| 2021/0290177 A1 | 9/2021 | Novak, Jr. |
| 2021/0290184 A1 | 9/2021 | Ahmed |
| 2021/0296008 A1 | 9/2021 | Novak, Jr. |
| 2021/0330228 A1 | 10/2021 | Olsen et al. |
| 2021/0386382 A1 | 12/2021 | Olsen et al. |
| 2021/0402110 A1 | 12/2021 | Pauley et al. |
| 2022/0039707 A1 | 2/2022 | Sharma et al. |
| 2022/0053892 A1 | 2/2022 | Al-Ali et al. |
| 2022/0071562 A1 | 3/2022 | Kiani |
| 2022/0096603 A1 | 3/2022 | Kiani et al. |
| 2022/0151521 A1 | 5/2022 | Krishnamani et al. |
| 2022/0218244 A1 | 7/2022 | Kiani et al. |
| 2022/0287574 A1 | 9/2022 | Telfort et al. |
| 2022/0296161 A1 | 9/2022 | Al-Ali et al. |
| 2022/0361819 A1 | 11/2022 | Al-Ali et al. |
| 2022/0379059 A1 | 12/2022 | Yu et al. |
| 2022/0392610 A1 | 12/2022 | Kiani et al. |
| 2023/0028745 A1 | 1/2023 | Al-Ali |
| 2023/0038389 A1 | 2/2023 | Vo |
| 2023/0045647 A1 | 2/2023 | Vo |
| 2023/0058052 A1 | 2/2023 | Al-Ali |
| 2023/0058342 A1 | 2/2023 | Kiani |
| 2023/0087671 A1 | 3/2023 | Telfort et al. |
| 2023/0110152 A1 | 4/2023 | Forrest et al. |
| 2023/0111198 A1 | 4/2023 | Yu et al. |
| 2023/0115397 A1 | 4/2023 | Vo et al. |
| 2023/0116371 A1 | 4/2023 | Mills et al. |
| 2023/0135297 A1 | 5/2023 | Kiani et al. |
| 2023/0138098 A1 | 5/2023 | Telfort et al. |
| 2023/0145155 A1 | 5/2023 | Krishnamani et al. |
| 2023/0147750 A1 | 5/2023 | Barker et al. |
| 2023/0210417 A1 | 7/2023 | Al-Ali et al. |
| 2023/0222805 A1 | 7/2023 | Muhsin et al. |
| 2023/0222887 A1 | 7/2023 | Muhsin et al. |
| 2023/0226331 A1 | 7/2023 | Kiani et al. |
| 2023/0284916 A1 | 9/2023 | Telfort |
| 2023/0284943 A1 | 9/2023 | Scruggs et al. |
| 2023/0301562 A1 | 9/2023 | Scruggs et al. |
| 2023/0346993 A1 | 11/2023 | Kiani et al. |
| 2023/0368221 A1 | 11/2023 | Haider |
| 2023/0371893 A1 | 11/2023 | Al-Ali et al. |
| 2023/0389837 A1 | 12/2023 | Krishnamani et al. |
| 2024/0016418 A1 | 1/2024 | Devadoss et al. |
| 2024/0016419 A1 | 1/2024 | Devadoss et al. |
| 2024/0047061 A1 | 2/2024 | Al-Ali et al. |
| 2024/0049310 A1 | 2/2024 | Al-Ali et al. |
| 2024/0049986 A1 | 2/2024 | Al-Ali et al. |
| 2024/0081656 A1 | 3/2024 | DeJong et al. |
| 2024/0122486 A1 | 4/2024 | Kiani |
| 2024/0180456 A1 | 6/2024 | Al-Ali |
| 2024/0188872 A1 | 6/2024 | Al-Ali et al. |
| 2024/0245855 A1 | 7/2024 | Vo et al. |
| 2024/0252046 A1 | 8/2024 | Jansen et al. |
| 2024/0260894 A1 | 8/2024 | Olsen |
| 2024/0267698 A1 | 8/2024 | Telfort et al. |
| 2024/0277233 A1 | 8/2024 | Al-Ali |
| 2024/0277280 A1 | 8/2024 | Al-Ali |
| 2024/0298920 A1 | 9/2024 | Fernkbist et al. |
| 2024/0306985 A1 | 9/2024 | Vo et al. |
| 2024/0324953 A1 | 10/2024 | Telfort |
| 2024/0380246 A1 | 11/2024 | Moran |
| 2024/0380247 A1 | 11/2024 | Moran |

FOREIGN PATENT DOCUMENTS

| | | |
|---|---|---|
| CA | 2 366 493 | 11/2002 |
| EP | 0 204 459 | 12/1986 |
| EP | 0 313 238 | 4/1989 |
| EP | 1 222 894 A2 | 7/2002 |
| EP | 1 222 894 A3 | 10/2003 |
| JP | 2003-521985 | 7/2003 |
| JP | 2004-329406 | 11/2004 |
| KR | 2012-0001261 | 1/2012 |
| WO | WO 96/031155 | 10/1996 |
| WO | WO 00/021433 | 4/2000 |
| WO | WO 01/003574 | 1/2001 |
| WO | WO 01/041634 | 6/2001 |
| WO | WO 02/089664 | 11/2002 |
| WO | WO 2010/135373 | 11/2010 |

OTHER PUBLICATIONS

U.S. Pat. No. 8,989,831, Disposable Components for Reusable Physiological Sensor, Mar. 24, 2015.
U.S. Pat. No. 9,895,107, Disposable Components for Reusable Physiological Sensor, Feb. 20, 2018.
U.S. Appl. No. 10,342,487, Disposable Components for Reusable Physiological Sensor, Jul. 9, 2019.
U.S. Appl. No. 16/425,592, Disposable Components for Reusable Physiological Sensor, filed May 29, 2019.
U.S. Appl. No. 13/571,910, Fingertip Pulse Oximeter, filed Aug. 10, 2012.
European Examination Report re EPO Application No. 06 83 8888.3, dated Sep. 27, 2011.
European Extended Search Report re EPO Application No. 11 16 9443.6, dated Sep. 12, 2011.
International Search Report and Written Opinion issued in PCT application No. PCT/US2010/035323, dated Aug. 13, 2010, in 16 pages.

(56) References Cited

OTHER PUBLICATIONS

International Search Report in PCT application No. PCT/US2006/046176, dated Nov. 29, 2006, in 4 pages.
Japanese Office Action re JP Application No. 2008-543525, dated Feb. 28, 2012.

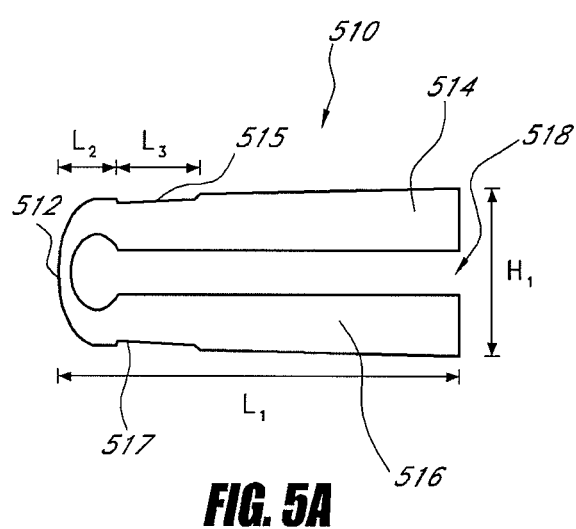 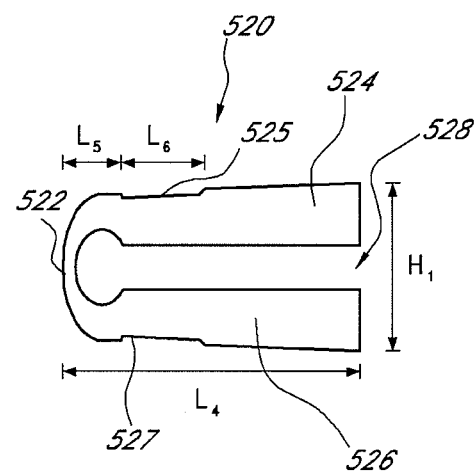
FIG. 5A  FIG. 5B

DISPOSABLE COMPONENTS FOR REUSABLE PHYSIOLOGICAL SENSOR

CROSS-REFERENCE TO RELATED APPLICATIONS

The present application is a continuation of U.S. patent application Ser. No. 16/425,592, filed May 29, 2019, which application is a continuation of U.S. patent application Ser. No. 15/864,389, filed Jan. 8, 2018, which application is a continuation of U.S. patent application Ser. No. 14/626,570, filed Feb. 19, 2015, which application is a continuation of U.S. patent application Ser. No. 12/782,651, filed May 18, 2010, which application claims the benefit of priority from U.S. Provisional Application No. 61/179,670, filed May 19, 2009. The entire contents of each of the above items are hereby incorporated by reference herein for all purposes.

FIELD OF THE DISCLOSURE

The present disclosure generally relates to disposable components of non-invasive physiological sensors.

BACKGROUND OF THE DISCLOSURE

Non-invasive physiological sensors are applied to the body for monitoring or making measurements indicative of a patient's health. One application for a non-invasive physiological sensor is pulse oximetry, which provides a noninvasive procedure for measuring the oxygen status of circulating blood. Oximetry has gained rapid acceptance in a wide variety of medical applications, including surgical wards, intensive care and neonatal units, general wards, and home care and physical training. A pulse oximetry system generally includes a physiological sensor having light emitters and a detector, such as one or more LEDs and a light sensor. The sensor is attached to a tissue site, such as a finger, toe, ear lobe, nose, hand, foot, or other site having pulsatile blood flow which can be penetrated by light from the emitters. The detector is responsive to the emitted light after attenuation by pulsatile blood flowing in the tissue site. The detector outputs a detector signal to a monitor which processes the signal to provide a numerical readout of physiological parameters such as oxygen saturation (SpO2) and pulse rate.

High fidelity pulse oximeters capable of reading through motion induced noise are disclosed in U.S. Pat. Nos. 6,770,028, 6,658,276, 6,157,850, 6,002,952 5,769,785, and 5,758,644, which are assigned to Masimo Corporation ("Masimo") and are incorporated by reference herein. Advanced physiological monitoring systems may incorporate pulse oximetry in addition to advanced features for the calculation and display of other blood parameters, such as carboxyhemoglobin (HbCO), methemoglobin (HbMet) and total hemoglobin (Hbt), total Hematocrit (Hct), oxygen concentrations and glucose concentrations, as a few examples. Advanced physiological monitors and corresponding multiple wavelength optical sensors capable of measuring parameters in addition to $SpO_2$, such as HbCO, HbMet and Hbt are described in at least U.S. patent application Ser. No. 11/367,013, filed Mar. 1, 2006, titled Multiple Wavelength Sensor Emitters and U.S. patent application Ser. No. 11/366,208, filed Mar. 1, 2006, titled Noninvasive Multi-Parameter Patient Monitor, assigned to Masimo Laboratories, Inc. and incorporated by reference herein. Further, noninvasive blood parameter monitors and optical sensors including Rainbow™ adhesive and reusable sensors and RAD57™ and Radical-7™ monitors capable of measuring $SpO_2$, pulse rate, perfusion index (PI), signal quality (SiQ), pulse variability index (PVI), HbCO and HbMet, among other parameters, are also commercially available from Masimo.

SUMMARY OF THE DISCLOSURE

Optical sensors are widely used across clinical settings, such as operating rooms, emergency rooms, post anesthesia care units, critical care units, outpatient surgery and physiological labs, to name a few. Use in these settings exposes sensors, and in particular reusable sensors, to the potential risks of contamination and the resulting spread of nosocomial (hospital-acquired) infections. Studies have suggested that visual inspection of sensors may not detect contamination. Further, while a low-level disinfection protocol of alcohol wipes, dilute bleach scrubs or distilled water wipes can be effective when done correctly, reusable sensors may still be at risk for bacteria including MRSA (methicillin resistant *Staphylococcus aureus*). MRSA causes skin infections and can occasionally spread to almost any other organ in the body, sometimes with life-threatening potential. It is therefore a priority among medical care facilities to prevent contamination of reusable sensors by foreign and infectious materials and to prevent the spread of nosocomial infections. A sterile sensor cover advantageously provides a sterile environment without interfering with sensor functionality and capability. For example, the sterile sensor cover may be substantially impermeable to infectious agents (e.g., bacteria) and substantially optically transparent or transmissive.

Further, sensor elements such as the detector, emitters and associated circuitry can be expensive parts of a patient monitoring system. Often, relatively inexpensive degradable portions of the sensor become damaged due to repeated use or frequent sterilization. For example, the portions of the sensor which contact the user's skin often become soiled or damaged after each use. In such cases, users often disconnect the sensor cable from the monitor and replace the entire sensor. Moreover, in certain cases, such as for portable applications, it is useful for a sensor to be integrated into the patient monitor housing and not be attached by a cable. In such cases the sensor may not be removable from the monitor.

Other attempted solutions that include sensors with flexible, adhesive substrates having disposable and reusable portions. The disposable portion generally includes the adhesive portion of the sensor, which can lose its tack. Such sensors generally wrap around and adhesively attach to the tissue site. However, non-adhesive sensors having rigid housings, such as clip type sensors which clamp onto the tissue of the patient, are also commonly used in pulse oximetry and other patient monitoring applications. These sensors include degradable components that can become damaged or soiled due to frequent use, such as upper and lower pads which contact the user's skin.

It is therefore desirable to decouple the degradable portions from the rest of the sensor so that the degradable portions can be replaced in a cost-effective manner, and the rest of the sensor can be reused. A disposable sensor cartridge according to embodiments of the disclosure is capable of being used with a non-invasive physiological sensor and protects the sensor from damage due to repeated use or sterilization.

In addition, incorrect alignment of a patient's tissue site with the sensor elements can lead to inaccurate results. For example, where the tissue site is a patient's finger, the emitter and detector should generally be aligned with the nail bed of the patient. Often it is difficult to determine whether the sensor is properly aligned because, for example, the sensor housing impedes the view of the tissue site in relation to the emitter and detector. In such cases, it may take the operator a significant amount of time to realize that a sensor is misaligned. As such, there is a need for a sensor which provides for robust tissue site alignment. Embodiments of the sensor cartridge are positionable on the user before placing the treatment site in the sensor, allowing for improved alignment of the treatment site.

In order to provide cost savings and allow for efficient use, it is also advantageous to be able to reuse sensors on different patients having tissue sites of various sizes, such as for both adults and children. The sensor cartridge of certain embodiments can be configured to allow a sensor to comfortably accommodate treatment sites of various sizes, such as for both adult and pediatric applications.

According to certain embodiments, a disposable sensor cartridge is provided for use with a noninvasive physiological sensor. The sensor cartridge can be capable of attaching to a tissue site and mating with a housing of the sensor. In certain embodiments, the sensor cartridge comprises a first portion comprising a first aperture configured to allow light emitted from one or more emitters of the sensor to travel through the first aperture such that the light is incident on a first region of a tissue site and travels through and is attenuated by body tissue of the tissue site. The attenuated light may exit the tissue site at a second region of the tissue site. In certain embodiments, the sensor cartridge also includes a second portion comprising a second aperture configured to allow the attenuated light to travel through the second aperture and to be received by a detector of the sensor. In some embodiments, the first and second portions coupled to define a cavity capable of receiving the tissue site. In certain embodiments, the sensor cartridge can also include an electrical component capable of electrical communication with the sensor. In some embodiments, the first portion is in contact with the first region while the cartridge is attached to the tissue site and the second portion is in contact with the second region while the cartridge is attached to the tissue site.

According to an aspect of the disclosure, a method of using a noninvasive physiological sensor having a housing is provided. The method can include providing a disposable sensor cartridge comprising a first portion comprising a first aperture and a second portion comprising a second aperture. In certain embodiments, the disposable sensor cartridge can also include an electrical component. The first portion and second portion may together define a cavity capable of receiving the tissue site. In certain embodiments, the method further includes attaching the sensor cartridge to the tissue site such that the tissue site is disposed within the cavity. The method according to some embodiments also includes mating the sensor cartridge with the sensor such that the sensor cartridge is disposed within a cavity of the sensor housing. In certain embodiments, mating of the sensor cartridge with the sensor is such that the electrical component is in electrical communication with a portion of the sensor.

In certain embodiments, a disposable sterile barrier is provided. The disposable sterile barrier may interpose a material impermeable to infectious biological substances between a tissue site and surfaces of a sensor configured to grasp the tissue site. The sensor may be configured to transmit optical radiation into the tissue site and to generate a signal responsive to the optical radiation after attenuation by pulsatile blood flow within the tissue site. In certain embodiments, the disposable sterile barrier comprises an optically transparent material that is substantially impermeable to infectious biological substances. The disposable barrier may comprise a first portion of the material formed such that the first portion can be interposed between a tissue site and a first surface of a reusable optical sensor proximate an emitter of the sensor. In certain embodiments, the disposable barrier may comprise a second portion of the material formed such that the second portion can be interposed between the tissue site and a second surface of the sensor proximate a detector of the sensor.

In certain embodiments, an optical sensing method of non-invasively measuring the constituents of pulsatile blood flow within a tissue site without substantial risk nosocomial infection by direct contact between a sensor and the tissue site. The optical sensing method may include providing a reusable optical sensor having an emitter disposed within a first housing and a detector disposed within a second housing, the emitter and detector in communication with a sensor cable, the first and second housings configured to be urged against opposite sides of a tissue site upon application of the sensor to the tissue site, the emitter configured to transmit optical radiation having one or more predetermined wavelengths into the tissue site and the detector configured to receive the optical radiation after attenuation by the tissue site. The sensor may be configured to generate one or more signals indicative of the attenuated radiation, the one or more signals transmitted via the sensor cable to a monitor configured to process the one or more signals to determine one or more physiological parameters of patient. The method may include applying a barrier so as to make physiological measurements without direct contact between the tissue site and the sensor. The barrier can be interposed between the tissue site and the first housing and interposed between the tissue site and the second housing upon application of the tissue site to the sensor, the barrier comprising material substantially impermeable to infectious substances and substantially transparent so as not to substantially distort the physiological measurements.

According to certain aspects of the disclosure, a disposable sterile barrier is provided comprising an elongate tube comprising a cavity. The elongate tube may comprise an open end and a closed end. In certain embodiments, the open end comprises an opening large enough to accommodate a reusable optical sensor. The cavity can be sized to fully enclose the reusable optical sensor and at least a portion of a sensor cable extending from the optical sensor. In some embodiments, the elongate tube comprises a material which is substantially optically transparent and substantially impermeable to infectious biological substances. In certain embodiments, the disposable sterile barrier may further include a fastener disposed proximate the open end of the elongate tube and configured to seal the open end of the elongate tube around the sensor cable.

BRIEF DESCRIPTION OF THE DRAWINGS

FIGS. 5A-B illustrate side views of two sensor cartridges of differing sizes according to an embodiment of the disclosure.

DETAILED DESCRIPTION

A sensor cartridge according to embodiments of the disclosure is capable of being used with a non-invasive physiological sensor. Certain embodiments of the sensor cartridge protect the sensor from damage, such as damage due to repeated use, reduce the need for sensor sanitization, or both. Further, embodiments of the sensor cartridge are positionable on the user before insertion in the sensor and allow for improved alignment of the treatment site with the sensor. In addition, the sensor cartridge of certain embodiments of the disclosure can be configured to allow a single sensor to comfortably accommodate treatment sites of various sizes such as for both adult and pediatric applications. The terms "sensor cover" and "sensor cartridge" are used throughout to describe various embodiments of the disclosure. The terms may be used interchangeably and are not intended to be limiting.

The tissue site of the illustrated embodiments is a finger and the following description therefore refers specifically to the tissue site as a finger for the purposes of clarity. This is not intended to be limiting and, as described herein, the sensor cartridge 110 of certain embodiments may be used with other types of tissue sites.

Figure 1:
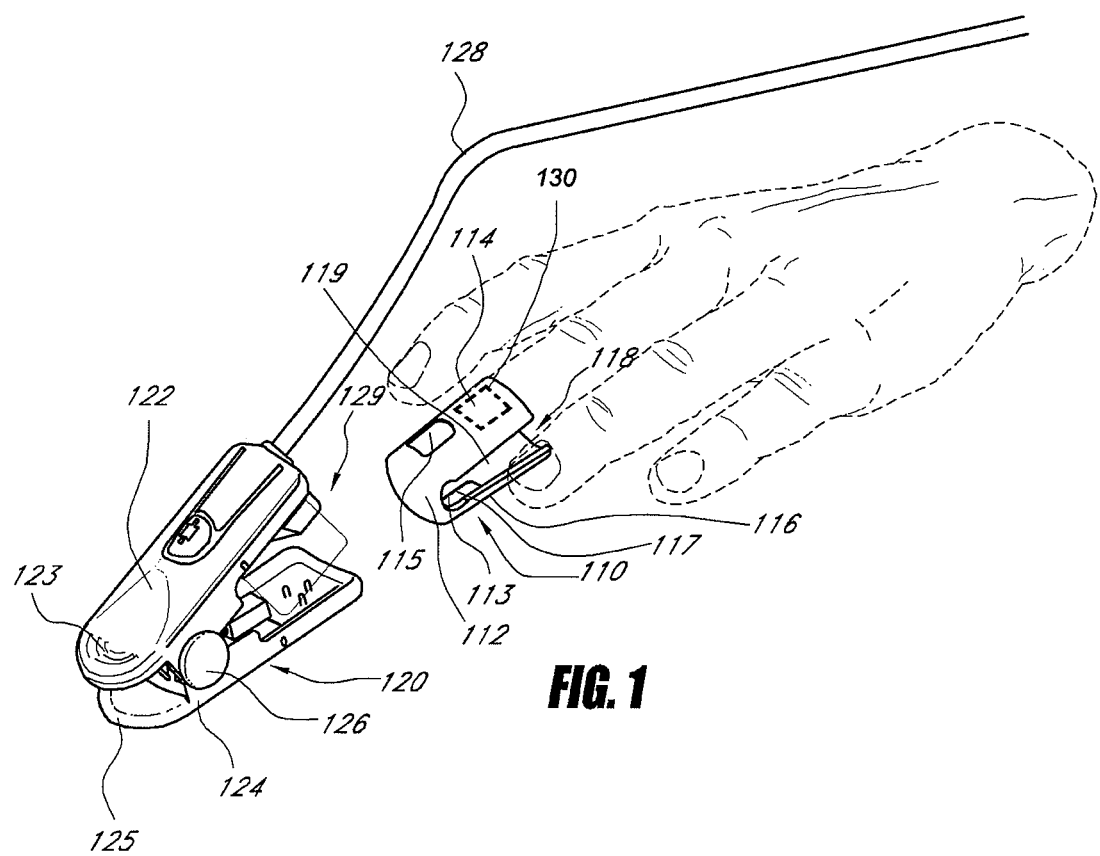
FIG. 1 is a perspective view of a sensor cartridge and associated sensor according to an embodiment of the disclosure.

FIG. 1 is a perspective view of a sensor cartridge 110 and associated sensor 120 according to an embodiment of the disclosure. A user can place a cartridge 110 on a finger of the patient and then insert the finger along with the attached cartridge 110 into a non-invasive physiological sensor 120.

The sensor 120 can be a clip-type sensor including an upper housing 122, a lower housing 124 and a hinge element 126. The upper and lower housings 122, 124 house electrical and/or optical components (not shown) of the non-invasive physiological sensor 120. For example, the upper and lower housings 122, 124 may house light emitters and a detector of a pulse oximeter sensor, such as one or more LEDs and a light sensor. The sensor 120 can be connected to a patient monitor (not shown) via a cable 128. For example, the detector outputs a signal to the monitor over the cable 128 which then processes the signal to provide a numerical readout of physiological parameters such as oxygen saturation (SpO2) and pulse rate.

After placing the sensor cartridge 110 on the finger, the user can attach the sensor 120 to the patient by applying pressure to the ends 123, 125 of the upper and lower housings 122, 124, forming a cavity 129 capable of receiving the tissue site. Once the patient inserts the tissue site along with the attached sensor cartridge 110 into the cavity 129, the pressure on the ends 123, 125 can be released such that the upper and lower housings 122, 124 come in contact with and secure the tissue site, allowing for accurate non-invasive physiological measurement.

Although disclosed with reference to the sensor of FIG. 1, an artisan will recognize from the disclosure herein a wide variety of oximeter sensors, optical sensors, noninvasive sensors, medical sensors, or the like that may benefit from the sensor cartridges disclosed herein. The sensor may not be a hinge type sensor but may instead, for example, include an integral housing having an annular ring type opening through which the patient inserts their finger. In various embodiments, the sensor may be adapted to receive a tissue site other than a finger such as a, toe, ear lobe, nose, hand, foot, or other site having pulsatile blood flow which can be penetrated by light from the emitter. In addition, the cartridge 110 may be used with a portable monitor and associated sensor components in certain embodiments. Such monitors, including the sensor components, can be integrated into a hand-held device such as a PDA and typically do not include cables or separate monitors. Portable monitors are often used by first responders in emergency situations, in part because of their portability and ease of use. As such, disposable cartridges 110 which can protect the sensor components according to embodiments herein can be of particular benefit when used with spot-check monitors. In addition, in emergency situations medical personnel must treat a large number of patients relatively quickly and it may therefore be difficult to sanitize sensors between patients. Disposable cartridges 110 described herein benefit medical personnel in such cases because a separate pre-sterilized cartridge 110 can be used for each patient.

Referring still to FIG. 1, the cartridge 110 includes an upper portion 114, a lower portion 116 and a hinge portion 112 which together form a cavity 118 capable of receiving a finger. The upper portion 114, lower portion 116 and hinge portion 112 are generally curved so as to accommodate the natural shape of the finger. A hinge cut-out 113 can be disposed on either side of the cartridge 110 near the hinge portion 112, allowing for the upper and lower portions 114, 116 to separate from each other by rotating about the hinge portion 112. To apply the cartridge to the finger, the upper portion 114 and lower portion 116 may be separated such that they rotate about the hinge portion 112 and the cavity 118 becomes large enough to comfortably receive the finger. Once the finger is placed in the cavity 118, the upper and lower portions 114, 116 are released, coming into contact with and releasably attaching to the finger. For example, in certain embodiments, the hinge portion 112 may provide a spring force which is transferred to the upper and lower portions 114, 116 when they are released such that they grab onto the finger. In some embodiments, the interior surface 119 of the cartridge 110 may include an adhesive substance such that the cartridge 110 is releasably attached to the finger or other tissue site. In other configurations, the cartridge 110 simply rests on the finger and there is not a separate attachment mechanism.

The upper portion 114 includes an upper aperture 115 and the lower portion 116 includes a lower aperture 117. The apertures 115, 117 generally allow for proper sensor operation. For example, the apertures 115, 117 allow for light from one or more emitters of the sensor 120 to contact the finger and for light attenuated by the tissue site to be received by a detector of the sensor 120.

Because the upper and lower sensor housings 122, 124 are often opaque, it can be difficult to determine whether or not a finger is properly aligned once it is placed in the sensor. The apertures 115, 117 can allow for proper alignment of the sensor cartridge 110 with respect to the finger prior to inserting the cartridge 110 and finger into the sensor 120. Proper alignment of the cartridge 110 with the finger can therefore improve the accuracy of measurements by helping to ensure that the finger will be properly aligned with respect to the sensor 120 elements upon mating of the cartridge 110 and sensor 120. In certain cases, medical personnel may not realize that an inaccurate measurement has occurred, or may not realize it until after an alarm on the sensor goes off, after removal of the sensor or after the patient has left the treatment facility. As such, proper alignment can also help reduce cost and save time.

The upper aperture 115 allows a user to visually determine whether the nail bed of a finger is properly aligned with the aperture 115. Proper alignment of the nail bed also ensures that the lower aperture 117 is properly aligned with the fleshy part of the underside of the finger. In addition, the user may visually determine that the underside of the finger is properly aligned by looking through the lower aperture 117. The finger with the properly aligned cartridge 110 can then be inserted into the sensor 120 such that the light from the emitters of the sensor 120 will be incident on the nail bed through the upper aperture 115. Further, the detector of the sensor 120 then receives attenuated light from the appropriate portion of the underside of the finger through the lower aperture 117. In other embodiments, the emitter of the sensor 120 is housed in the lower housing 124 and the detector is housed in the upper housing 122.

In certain embodiments, a film or other material (not shown) may be included in one or more of the apertures 115, 117. For example, in one embodiment, translucent plastic film is placed in the apertures 115, 117 such that the properties of the emitted and attenuated light passing through the apertures are not affected by the material. In other embodiments, material is used which does affect the optical properties. For example, an optical film which filters out particular wavelengths of light is used in some embodiments.

Tactile feedback elements (not shown) may indicate proper alignment of the cartridge instead of, or in addition to, the apertures 115, 117. For example, one or more of the upper and lower portions 114, 116 may include small protrusions which indicate to the patient whether the cartridge 110 is properly aligned. In one embodiment, for example, protrusions on either side of the finger indicate to the patient that the cartridge 110 is centered on the finger and a protrusion near the hinge portion 112 indicates that the finger is inserted appropriately deep into the cartridge 110. Other tactile elements such as, for example, recesses, may be used in other embodiments.

In certain embodiments, the properties of the interior 119 of the cartridge 110 allow for proper and efficient calibration of the sensor 120. For example, the interior 119 of the cartridge may be a highly reflective color such as white. The interior 119 may also have a glossy texture in certain embodiments, which can also aid in the calibration of the sensor.

As discussed, the sensor cartridge 110 is configured to mate with the sensor 120. For example, the cartridge 110 of FIG. 1 mates in a friction fit with the sensor 120. To release the cartridge 110 from the sensor 120 after use, the user opens the sensor 120 clip, thereby relieving the pressure on the cartridge and tissue site from the upper and lower housings 122, 124. The user can then readily pull the tissue site and cartridge 110 out of the cavity 129. As will be appreciated by skilled artisans from the disclosure provided herein, other types of mating and release mechanisms are possible. For example, snap-fit mating configurations such as the one described below with respect to FIG. 3 can be used. In some embodiments, a male or female track on the cartridge 110 fits into a corresponding male or female track on the sensor 120, as appropriate. A button or lever release mechanism may be used in certain embodiments. In some embodiments, the cartridge 110 may automatically release when the sensor 120 clip is opened.

The sensor cartridge 110 or a portion thereof can be constructed of urethane rubber plastic in certain embodiments. In various other configurations, as will be appreciated from the disclosure herein, the cartridge 110 may be made of other appropriate materials such as Acrylonitrile Butadiene Styrene ("ABS") or other types of rubber or plastic materials. The cartridge 110 is formed with biodegradable material in certain embodiments.

The general structure of the sensor cartridge 110 may differ in various configurations. For example, the cartridge may not be an integral molded piece as shown in the embodiment of FIG. 1 and may instead include separate pieces as discussed with respect to FIG. 3 below.

In an example scenario, once the user attaches the properly aligned sensor cartridge 110 to the tissue site and applies the sensor 120 as discussed above, medical personnel take a measurement of one or more physiological parameter of the patient using the sensor 120. The patient then removes the tissue site from the sensor 120 along with the attached cartridge 110 as discussed and the patient or medical personnel may dispose of the cartridge 110. Those of skill in the art will recognize from the disclosure herein various ways of using the cartridge 110. For example, the cartridge 110 of certain embodiments may be mated with the sensor 120 before application to the tissue site. Moreover, the cartridge may be used more than once. For example, the cartridge 110 may be used several times by the same patient before disposal. In some embodiments, the cartridge 110 may be sterilized between uses.

In certain embodiments, the sensor cartridge 110 is configured to be in electrical communication with the sensor 120. For example, the sensor cartridge 110 can also include one or more electronic components 130 and one or more coupling portions (not shown) which may be electrically coupled to the sensor 120. For example, the coupling portions may comprise one or more electrical contacts (e.g., solder pads), electrical connectors (e.g., a socket and pin type connector), and the like. The electronic components 130 may include one or more information elements in certain embodiments. The information element may comprise one or more memory devices, such as, for example, one or more EPROMs or EEPROMs (e.g., those commercially available from Dallas Semiconductor), other memory or processing devices, combinations of the same, or the like. In some embodiments, the information element includes a conductor, a resistor, a single wire addressable memory device, or the like. In general, the information element may include a read-only device or a read and write device. The information element may advantageously comprise a resistor, an active network, or any combination of the foregoing. The information element may include data accessible by the sensor 120 and/or attached patient monitor to accomplish quality control, use monitoring, combinations of the same, or the like. For example, the information element may provide identification information to the system (e.g., the sensor 120 and/or monitor) which the system uses to determine whether the cartridge is compatible with the system. In an advantageous embodiment, the monitor reads the information element to determine one, some or all of a wide variety of data and information, including, for example, a type of patient, cartridge manufacturer information, life data indicating whether the cartridge has been used and/or should be replaced, encryption information, keys, indexes to keys or has functions, or the like monitor or algorithm upgrade instructions or data, some or all of parameter equations, information about the patient, age, sex, medications, and other information that can be useful for the accuracy or alarm settings and sensitivities, trend history, alarm history, sensor life, or the like.

The information element may be positioned on the hinge portion 112. For example, in one embodiment the information element be embedded in the cartridge 112 material of the hinge portion 112 and is electrically coupled via a connector extending from the hinge portion 112 which mates with a corresponding connector on the interior of the sensor 120. Skilled artisans will recognize from the disclosure provided herein a variety of configurations for the placement of the information element. For example, in various embodiments, the information element may be located on one or more of the inner surface of the cartridge 110, the outer surface of the cartridge 110, or embedded within the cartridge 110 material. Moreover, the information element may be positioned on the hinge portion 112, the upper portion 114, the lower portion 116, or a combination thereof.

The information element may advantageously store some or all of a wide variety of data and information, including, for example, information on the type or operation of the sensor cartridge, buyer or manufacturer information, software such as scripts, executable code, or the like, sensor cartridge 110 life data indicating whether the sensor cartridge 110 has expired and should be replaced, encryption information, etc. or monitor or algorithm upgrade instructions or data. In various configurations, the information element may advantageously configure or activate the monitor, monitor algorithms, monitor functionality, or the like based on some or all of the foregoing information. For example, without authorized data accessible on the information element, quality control functions may inhibit functionality of the monitor. Likewise, particular data may activate certain functions while keeping others inactive. For example, a particular cartridge 110 may be compatible for use in measuring one type of physiological parameter of a set of physiological parameters the monitor is capable of measuring. In such a circumstance, the monitor may only activate measurement of the one type of physiological parameter based on the data accessible from the information element. Further information regarding information elements and systems and methods for monitoring sensor life can be found in U.S. Publication No. 2008/0088467, which is hereby incorporated in its entirety by reference herein.

While disclosed with respect to the cartridge 110 of FIGS. 1-2, any of the cartridges described herein, such as the cartridges 300, 510, 520, 610, 620, 1100, 1200 described below of FIGS. 3-6 and FIGS. 11-12 may include one or more information elements. Likewise, any of the sensor covers disclosed herein, such as the sensor covers 700, 800 of FIGS. 7-10 may include an information element.

Figure 2A:
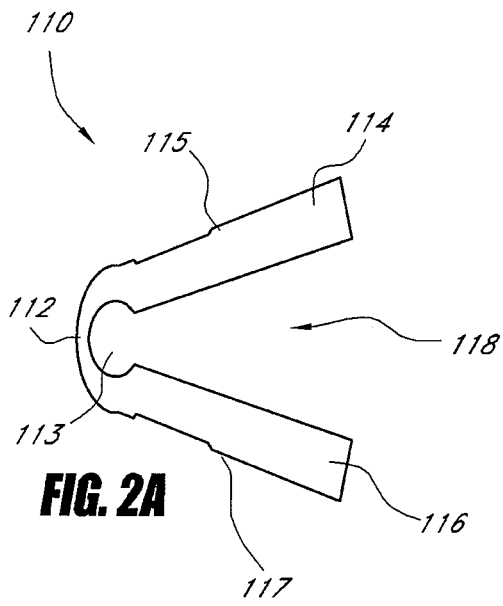
FIGS. 2A-D are side hinged-open, side hinged-closed, top and bottom perspective views, respectively, of the sensor cartridge of FIG. 1.
Figure 2B:
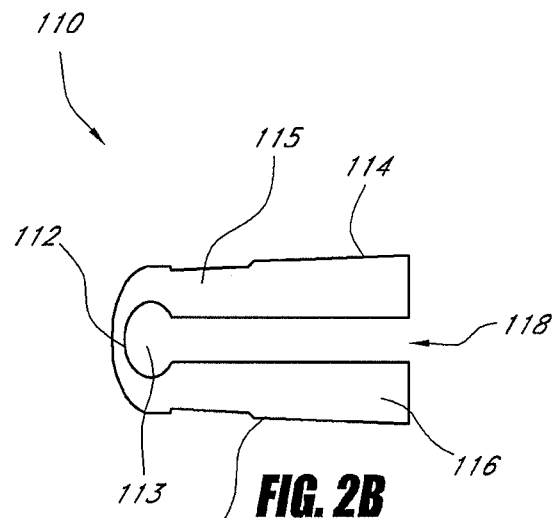
Figure 2C:
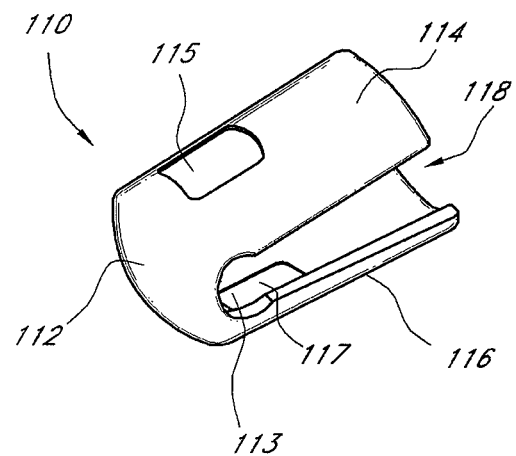
Figure 2D:
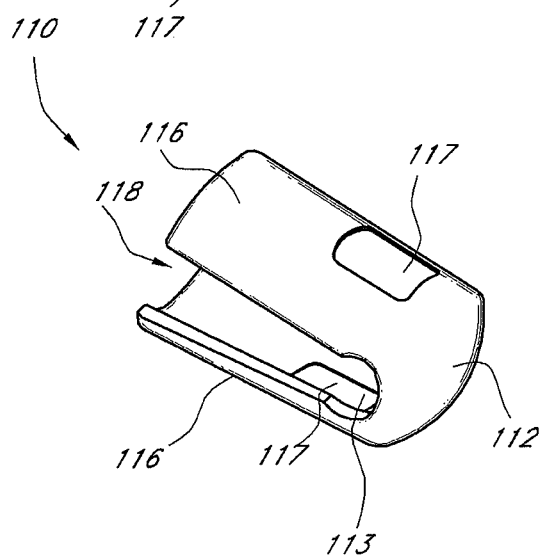
Figure 3A:
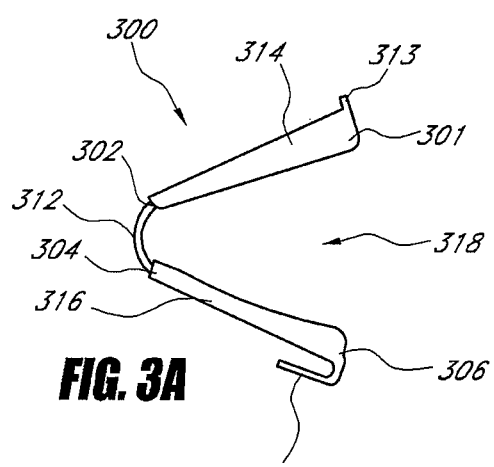
FIGS. 3A-D are side hinged-open and side hinged-closed views, top and bottom perspective views, respectively, of a sensor cartridge according to another embodiment of the disclosure.
Figure 3B:
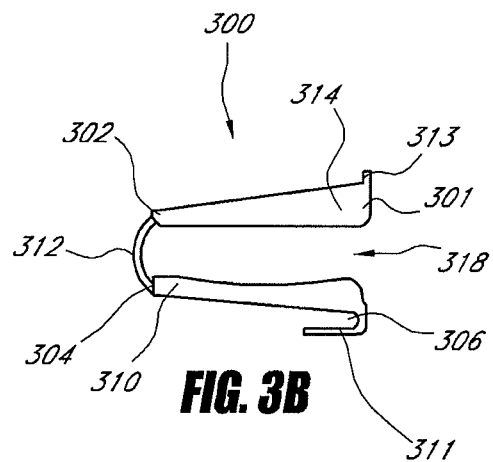
Figure 3C:
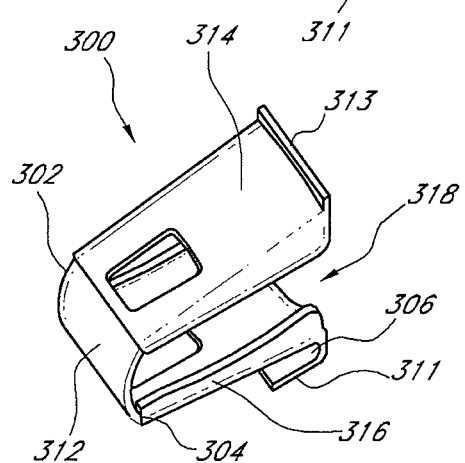
Figure 3D:
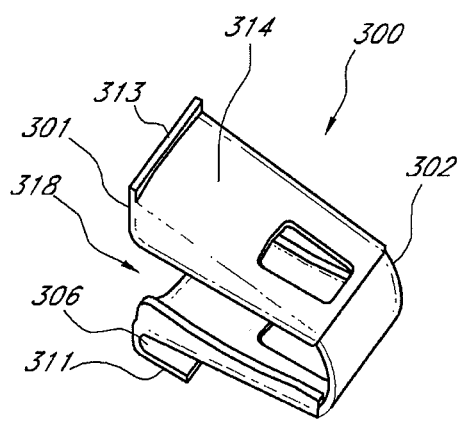

FIGS. 2A-D are side hinged-open, side hinged-closed, top-right perspective and top-left perspective views, respectively, of the sensor cartridge of FIG. 1. As discussed above, the upper portion 114 and lower portion 116 may be separated such that they rotate about the hinge portion 112 and the cavity 118 becomes large enough to comfortably receive the finger (FIG. 2A). Once the finger is placed in the cavity 118, the upper and lower portions 114, 116 can be released, coming into contact with and releasably attaching to the finger (FIG. 2B). The right and left sides of the cartridge 110 of the illustrated embodiment are symmetrical. As shown by FIGS. 2C-D, the top and bottom are also symmetrical. In other embodiments, the left and right sides and/or the top and bottom may be shaped differently, such as, for example, to accommodate asymmetric properties of the finger or other tissue site.

FIGS. 3A-D are side hinged-open and side hinged-closed views, top-right perspective and top-left perspective views, respectively, of a sensor cartridge 300 according to another embodiment of the disclosure. The cartridge 300 includes an upper portion 314, a lower portion 316 and a hinge portion 312, which are three separate pieces. As shown, the hinge portion 312 attaches to the back 302 of the upper portion 314 and the back 304 of the lower portion 316, forming a cavity 318 capable of receiving a finger of a patient. The hinge portion 312 may attach to the upper and lower portions 312, 314 with glue, may be formed integrally with the upper and lower portions 312, 314, or may be connected in some other manner. As shown with respect to FIGS. 3C-D, the cartridge 110 further includes upper and lower apertures 315, 317, which may be similar in structure and function to the apertures 115, 117 described above with respect to FIGS. 1-2.

Figure 4:
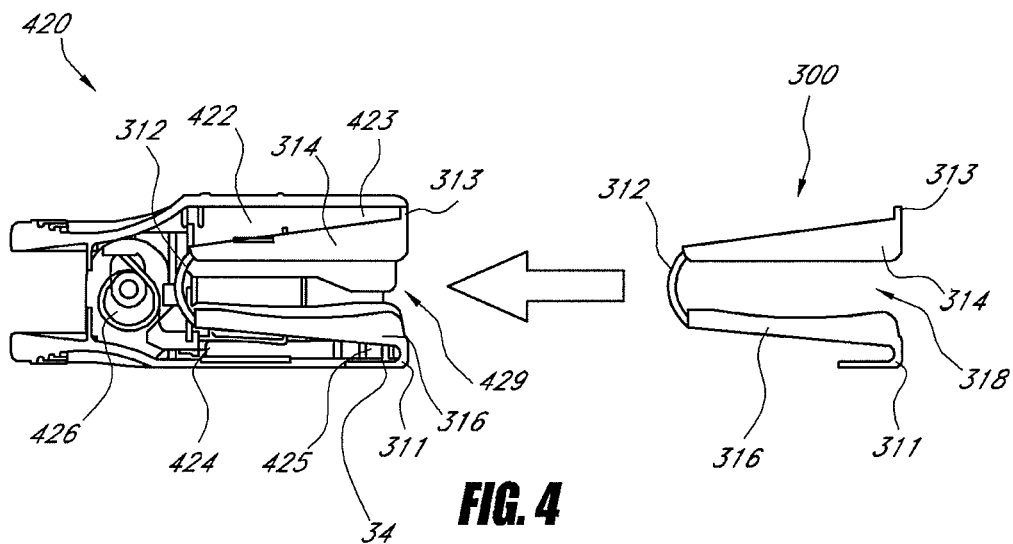
FIG. 4 illustrates the mating of the sensor cartridge of FIG. 3 with a sensor.

FIG. 4 illustrates the mating of the sensor cartridge of FIG. 3 with a sensor 420 (shown in a cross-sectional view). The sensor 420 may be similar in structure and function to the sensor 120 of FIG. 1, for example, and can include an upper housing 422, a lower housing 424 and a hinge portion 426 which form a cavity 429. One or more securing features may be included on the cartridge 300 to secure the cartridge 300 with the one or more corresponding securing features on the sensor 420 upon mating to secure the cartridge to the sensor 420 and/or ensure the correct position of the cartridge 300 within the sensor 420. Referring to FIGS. 3 and 4, for example, the attachment arm 311 is configured to secure the cartridge 300 in place when applied to the sensor 420. Upon application to a sensor 420 the front portion 425 of the lower housing 424 of the sensor 420 may occupy the space defined by the attachment arm 311 and the underside of the lower portion 316 of the cartridge 300. The attachment arm 311 helps to releasably secure the sensor 420, via a friction fit, for example. One or more other features, such as the lip 313 disposed on the upper portion 314 of the cartridge 300 can be included to further secure the cartridge 300 in the sensor 420. Upon insertion of the cartridge 300 into the sensor 420, the front portion 423 of the upper housing 422 abuts the lip 313. Accordingly, the lip 313 can help ensure that the cartridge 300 is positioned appropriately deep within the sensor 420.

The shape of the cartridge 300 may be configured to secure the cartridge 300 and/or ensure proper positioning of the cartridge 300 upon mating with the sensor 420. For example, as shown in FIGS. 3-4, the upper portion 314 and/or the lower portion 316 can be sloped such that they thicken towards the front 301 of the cartridge 300. Upon insertion, the sloping feature can provide a friction fit with the corresponding portions of the sensor 420.

As will be appreciated by skilled artisans from the disclosure provided herein, various attachment and positioning mechanisms may be used. For example, the attachment arm 311 may further include a protrusion or other feature which may fit into a corresponding feature, such as a recess (not shown), on the underside of the lower housing 424 of the sensor 420. In other configurations, the features may be reversed. For example, the protrusion may be on the lower housing 424 and the recess may be included on the attachment arm 311 of the cartridge 300.

FIGS. 5A-B illustrate side views of two sensor cartridges 510, 520 of differing sizes according to embodiments of the disclosure. The sensor cartridges 510, 520 may be similar in structure and function to the cartridge 100 of FIGS. 1-2 and include upper portions 514, 524, lower portions 516, 526, hinge portions 512, 522, cavities 518, 528, upper apertures 515, 525 and lower apertures 517, 527, respectively. The cartridges 510, 520 are configured to configured to accommodate treatment sites of various sizes, such as for both adult and pediatric applications. For example, the length $L_1$ of the cartridge 510 of FIG. 5A is larger than the corresponding length L4 of the cartridge 520 of FIG. 5B. Additionally, the upper and lower apertures 515, 517 of the cartridge 510 of FIG. 5A are set back a length L2 from the rear of the cartridge 510 which is relatively large in comparison to the length L5 that the upper and lower apertures 525, 527 of cartridge 520 of FIG. 5B are set back from the rear of the cartridge 520. The length L3 of the upper and lower apertures 515, 517 of the cartridge 510 of FIG. 5A is relatively large in comparison to the length L6 of the upper and lower apertures 525, 527 of the cartridge 520 of FIG. 5B.

The cartridge 510 is configured accommodate a larger finger than the cartridge 520. For example, the cartridge 510 may be used in adult applications and the cartridge 520 may be used in pediatric applications. A pediatric patient, for example, may have a nail bed that is set back a relatively short distance from the tip of the finger in comparison to an adult patient. As such, the shorter set back length L5 may be appropriate for a pediatric patient while the length L2 may be appropriate for an adult patient. A pediatric patient may also have a relatively smaller nail bed than an adult patient such that the smaller length L6 appropriately accommodates a pediatric patient while the length L3 may more appropriately accommodate an adult patient. Finally, pediatric patients typically have shorter fingers than adult patients such that the shorter overall cartridge length L4 may be appropriate for a pediatric patient while the longer length $L_1$ may be more appropriate for adult patients.

As shown, the external profile of the cartridges 520, 521, characterized in part by the maximum height of the cartridges 520, 521 $H_1$ may be the same. As such, the cartridges 520, 521 may mate with a single sized sensor, thereby reducing cost and complexity. One of skill in the art will recognize from the disclosure herein other configurations. Some of the lengths which are shown as different in the embodiments 510, 520 of FIGS. 5A-B may be the same in alternative configurations. For example, in various embodiments, one or more of the pairs of lengths L1 and L4, L2 and L5, L3 and L6 may be the same.

Figure 6A:
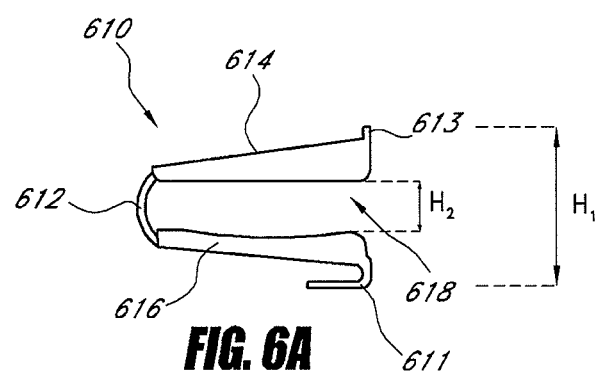
FIGS. 6A-B illustrate side views of two sensor cartridges of differing sizes according to another embodiment of the disclosure.
Figure 6B:
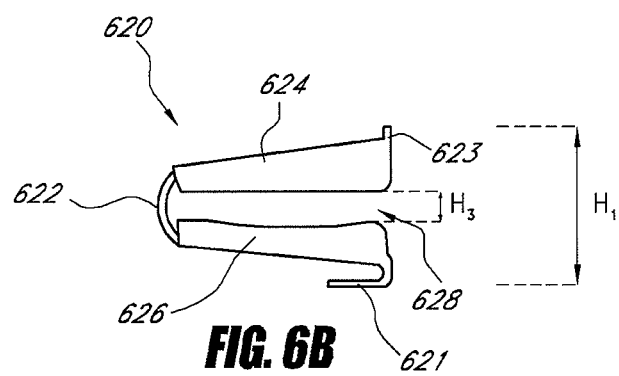

FIGS. 6A-B illustrate side views of two sensor cartridges 610, 620 of differing sizes according to embodiments of the disclosure. The sensor cartridges 610, 620 may be similar in structure and function to the cartridge 300 of FIG. 3 and include upper portions 614, 624, lower portions 616, 626, hinge portions 612, 622, cavities 618, 628, attachment arms 611, 621 and lips 613, 623 respectively. The cartridges 610, 620 are configured to configured to accommodate treatment sites of various sizes, such as for both adult and pediatric applications. For example, the upper and lower portions 614, 616 of the cartridge 610 are thinner than the corresponding portions 624, 626 of the cartridge 620 and define a relatively large cavity 618, characterized in part by the length $H_2$. On the other hand, the upper and lower portions 624, 626 of the cartridge 620 are relatively thick and define a relatively small cavity 628, characterized in part by the length $H_3$. As such, the cartridge 610 is configured accommodate a larger finger than the cartridge 620. For example, the cartridge 610 may be used in adult applications and the cartridge 620 may be used in pediatric applications.

As shown, the external profile of the cartridges 620, 621, characterized in part by the maximum height of the cartridges 620, 621 $H_1$ may be the same. As such, the cartridges 620, 621 may mate with a single sized sensor, thereby reducing cost and complexity. One of skill in the art will recognize from the disclosure herein other configurations. In some embodiments, the hinge portions 612, 614 are also shaped to accommodate tissue sites of various sizes. In some configurations, the upper portion, the lower portion and/or the hinge portion of the sensor cartridge are constructed of a resilient material (e.g., a spongy material) which conforms to the shape of the finger such that a sensor cartridge of a single size can accommodate tissue sites of multiple sizes. In some embodiments in which the opening of the cartridge is generally circular, the circumference of the opening through which the patient inserts their finger into the cavity 518 is larger than the opening of the cartridge 528.

Figure 7:
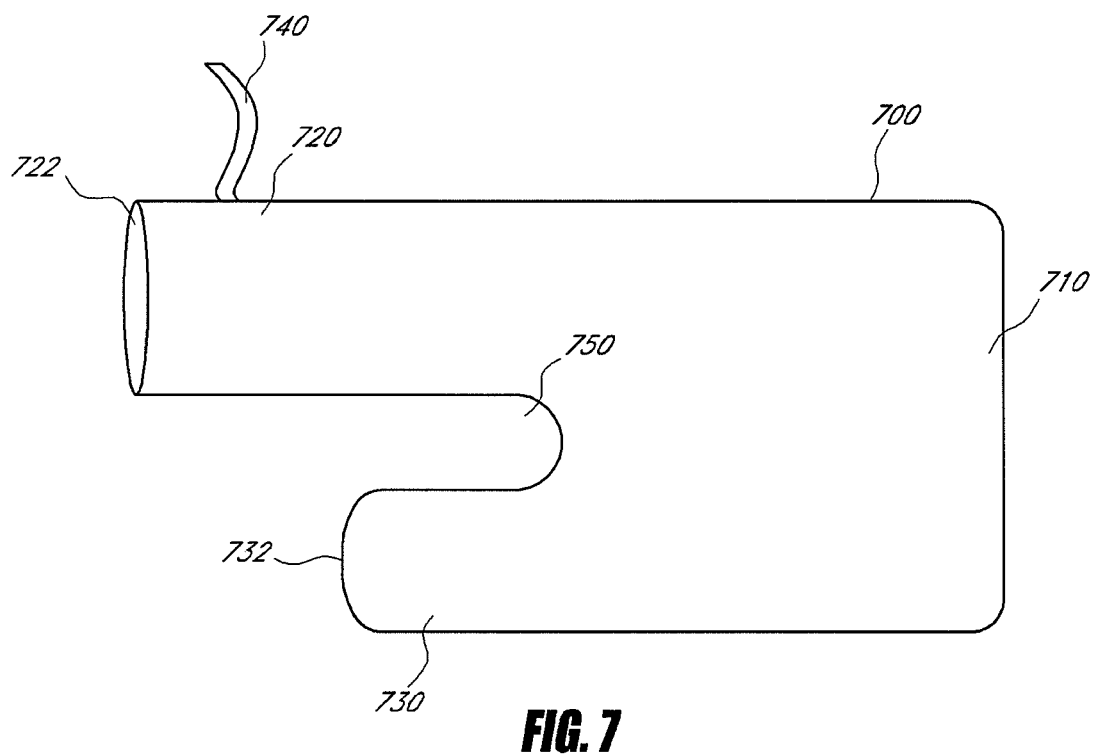
FIG. 7 is a side perspective view of a generally boot-shaped enclosure embodiment of a sterile sensor cover.
Figure 8:
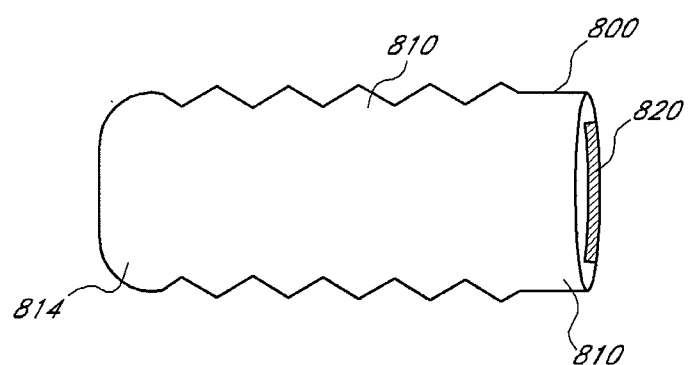
FIG. 8 is a side perspective view of a generally tube-shaped enclosure embodiment of a sterile sensor cover.

FIGS. 7-8 illustrate two embodiments of a sterile cover 700, 800 each advantageously configured to enclose a reusable sensor 120 (FIG. 1). In this manner, a patient's tissue site, such as a finger, can be inserted into the sensor and a physiological measurement made without contamination of the sensor or the patient. The sensor and the patient are thus advantageously protected from exposure to infectious agents such as MRSA.

As shown in FIG. 7, a boot-shaped cover 700 defines an enclosure having a generally tubular leg 720 and a smaller, generally tubular foot 730 both extending from a cross-member 710. In some embodiments, the cross-member 710 is sealed or substantially sealed. The leg 720 has an open end 722 of sufficient diameter to receive a reusable sensor 120, as described with respect to FIGS. 9A-B, below. The foot 730 has a closed end 732 of sufficient diameter to receive the lower housing 124 of a reusable sensor 120, as described with respect to FIGS. 9C-D, below. A tie 740 wraps around the open end 722 so as to close that end around the sensor cable 128. In one embodiment, the tie 740 is a self-adhesive tie, for example. In an embodiment, the tie 740 wraps around the open end 722 so as to seal the end around the sensor cable 128. A gap 750 between the leg 720 and foot 730 of the cover 700 defines a space configured to accommodate a finger-tip within the sensor 120.

As shown in FIG. 8, a tube-shaped cover 800 defines an enclosure having a generally cylindrical body 810 with an open end 812 and a closed end 814. The open end 812 is of sufficient diameter to receive first the lower housing 124 followed by the upper housing 122 of a reusable sensor 120, as described with respect to FIGS. 10A-D, below. A self-adhesive strip 820 disposed internal to the body 810 proximate the open end 812 closes the open end 812 around the sensor cable 128. In one embodiment, for example, the open end 812 forms a seal around the sensor cable 128. In an embodiment, the covers 700, 800 include of an optically transparent or substantially transparent material so as to negligibly attenuate or otherwise negligibly distort those wavelengths in the red and infrared spectrum utilized in pulse oximeters or otherwise for the measurement of blood constituents. For example, the covers 700, 800 may be substantially optically transmissive.

As used herein, the term "tube" is used to describe a generally elongate member comprising a cavity and may include an open end and a closed end, for example. As used herein, a tube may have a variety of shapes and characteristics. For example, the tube 800 of various may comprise a cylindrical, rectangular, ovular, triangular, or some other cross-sectional shape, or may be generally deformable.

Figure 9A:
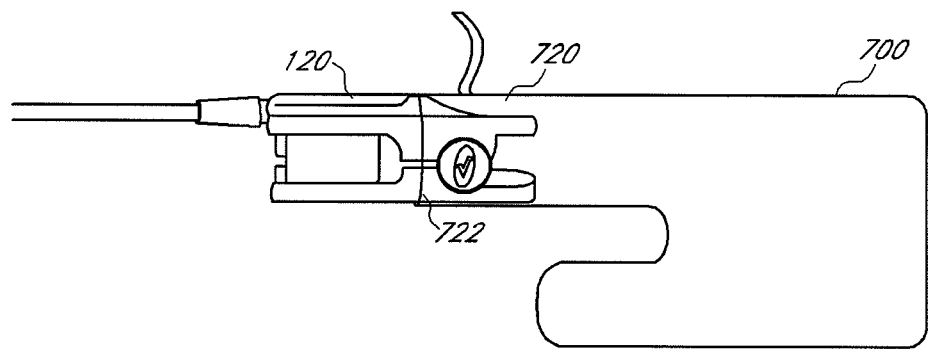
FIGS. 9A-F illustrate enclosing a reusable sensor with the boot-shaped enclosure and sealing the end with an attached tie.
Figure 9B:
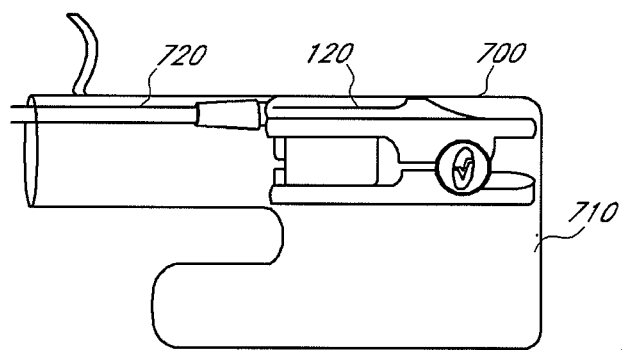
Figure 9C:
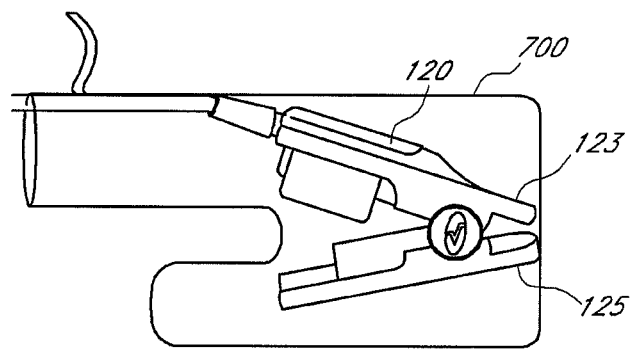
Figure 9D:
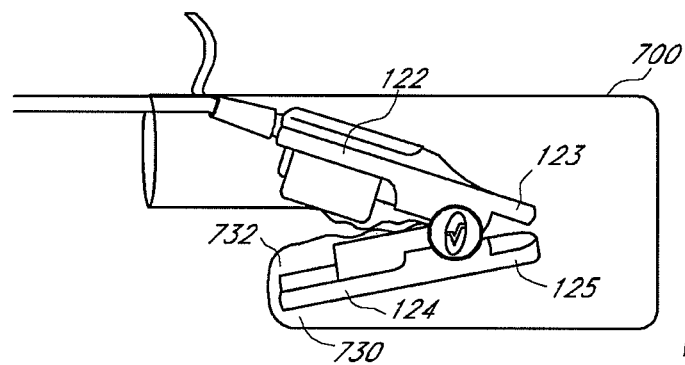
Figure 9E:
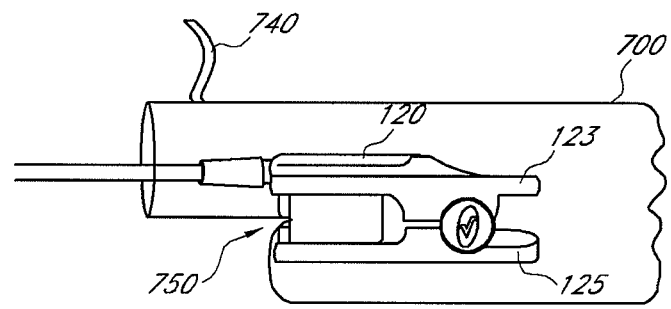
Figure 9F:
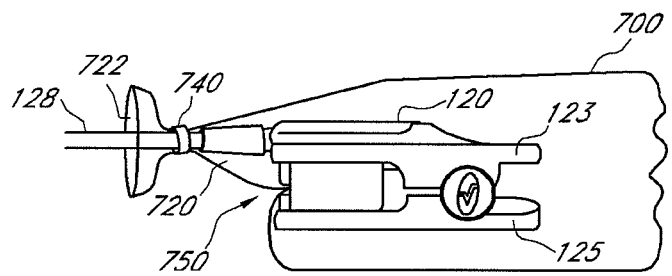

FIGS. 9A-F illustrate the use of a sterile cover 700 embodiment to enclose a reusable sensor 120, thereby advantageously protecting the sensor from contamination and the patient from exposure to infectious agents. A reusable sensor 120 in its normally closed position is initially inserted into the open end 722 of the cover 700 (FIG. 9A). The sensor 120 is then pushed through the length of the leg 720 until, for example, the sensor abuts the wall of the cross-member 710 (FIG. 9B). The sensor grips 123, 125 are pressed from outside the cover 700 so as to move the sensor 120 to its open position (FIG. 9C). While maintaining pressure on the grips 123, 125, the sensor lower housing 124 slides into the foot 730 until it abuts the closed end 732 (FIG. 9D). Pressure is released from the grips 123, 125 so that the sensor 120 returns to its closed position over the gap 750 (FIG. 9E). The tie 740 is wrapped around the leg 720 so as to close-off the end 722 tightly around the sensor cable 128 (FIG. 9F). The covered sensor 120 is now ready for single-patient use by squeezing the grips 123, 125 to open the sensor and by inserting a patient finger into the cover gap 750, which is now disposed inside the sensor 120, between the emitters and detector.

Figure 10A:
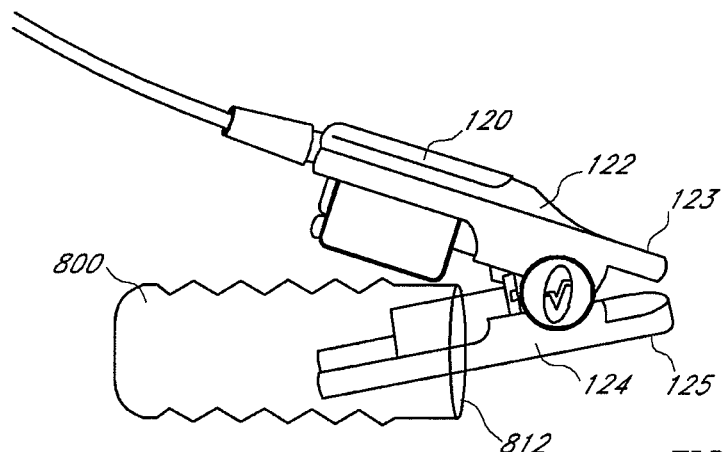
FIGS. 10A-E illustrate enclosing a reusable sensor with the tube-shaped enclosure and sealing the end with an adhesive strip.
Figure 10B:
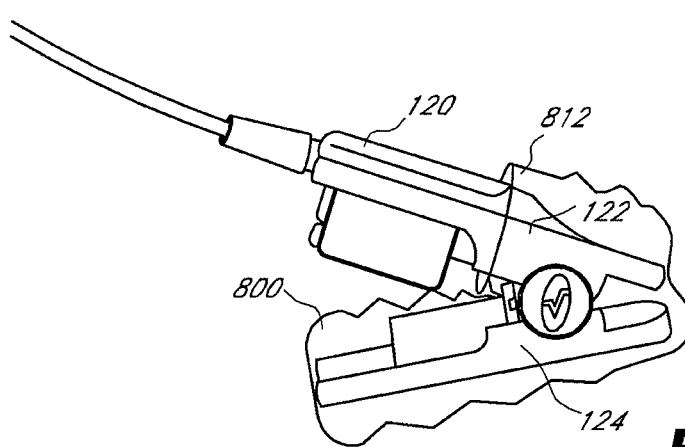
Figure 10C:
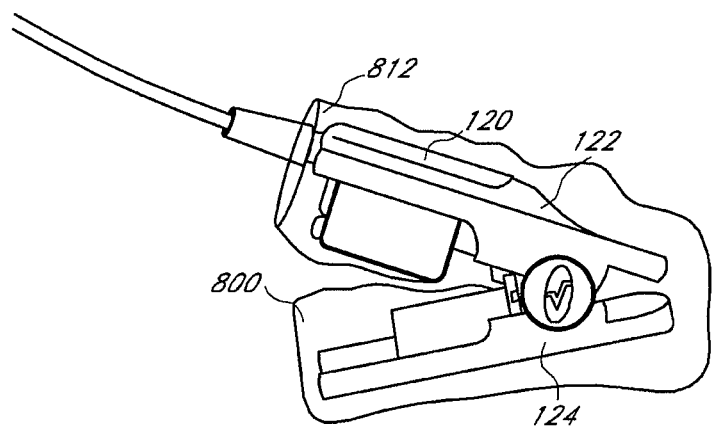
Figure 10D:
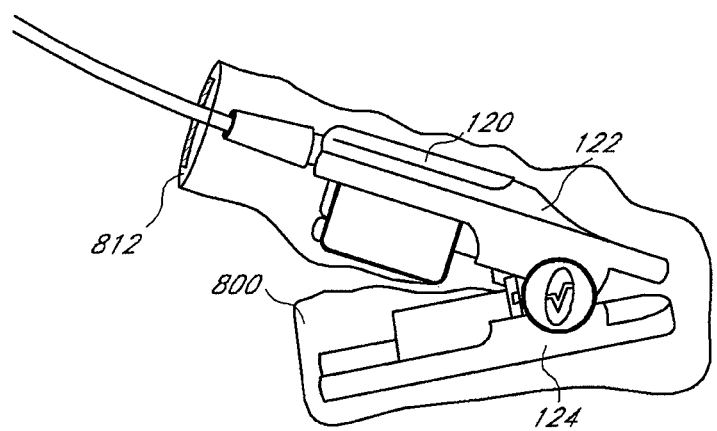
Figure 10E:
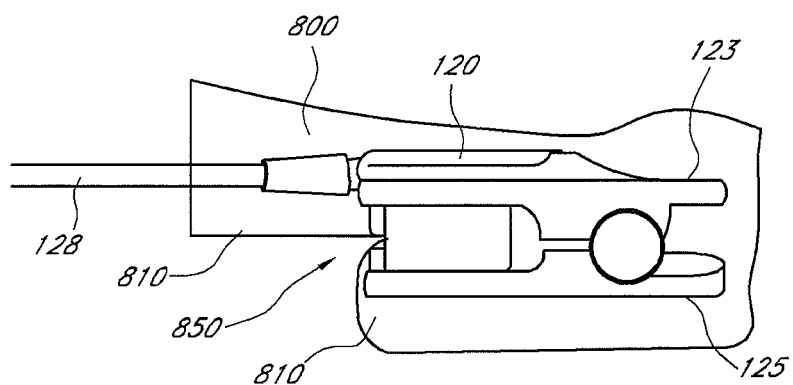

FIGS. 10A-E illustrate the use of another sterile cover 800 embodiment to enclose a reusable sensor 120, likewise substantially protecting the sensor and patient from contamination and/or infectious agents. Sensor grips 123, 125 are pressed to place the sensor 120 in an open position (FIG. 10A). The cover 800 may be initially in an "accordion" state or otherwise folded, rolled or compressed, or otherwise collapsible to a reduced overall length. The cover opening 812 is slipped over the lower housing 124 (FIG. 10A). Maintaining the sensor 120 in the open position, the cover 800 is unfolded or otherwise extended in length as the opening 812 is pulled over the grips 123, 125 and onto the upper housing 122 (FIG. 10B). The cover opening 812 is pulled further along the upper housing 122 and onto the sensor cable 128 (FIGS. 10C-D). The sensor grips 123, 125 are released so that the sensor 120 returns to its normally closed position (FIG. 10E). The self-adhesive strip 820 just inside the opening 812 is then exposed, such as by peeling back and removing a liner, and the opening 812 is securely closed around the cable 128 (FIG. 10E). The covered sensor 120 is now ready for single-patient use by squeezing the grips 123, 125 to open the sensor and by inserting 850 a patient finger into the sensor between the folded over wall 810 portions of the cover 800 (FIG. 10E). This places the patient's fingertip inside the sensor 120, between the emitters and detector.

Skilled artisans will recognize a variety of alternatives sensor covers 700, 800 from the disclosure provided herein. For example, in other embodiments, the covers 700, 800 may include one or more apertures such as one or more of the apertures described herein. The covers 700, 800 may comprise a rigid or semi-rigid material. Moreover, the covers 700, 800 may be used in addition to a cartridge such as one or more of the cartridges described herein with respect to FIGS. 1-6 and 11-12. In one alternative embodiment, the cover 700, 800 may extend beyond the sensor 120 along some length of the cable 128. For example, the cover 700, 800 may extend substantially along the entire cable to the monitor in one embodiment. In another embodiment, the cover 700, 800 may extend partially along the cable 128.

Figure 11A:
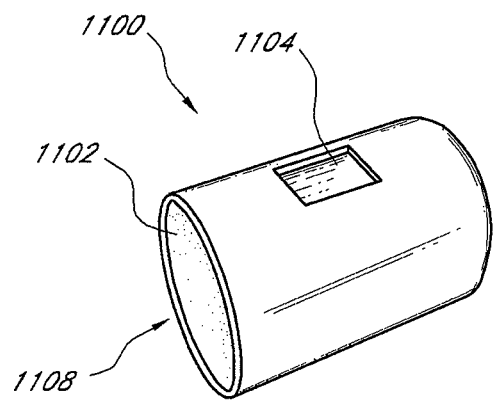
FIGS. 11A-B illustrate top front and bottom rear perspective views, respectively, of a sensor cartridge according to an embodiment of the disclosure.
Figure 11B:
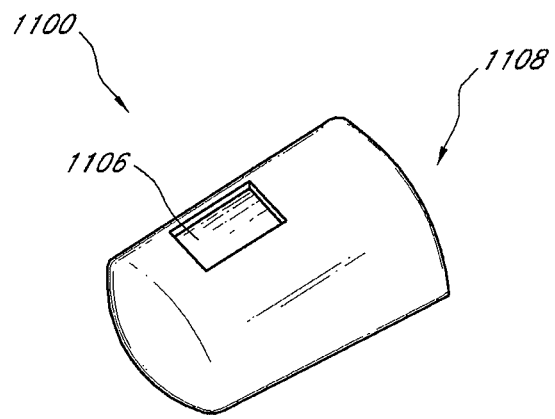

FIGS. 11A-B illustrate top front and bottom rear perspective views, respectively, of a sensor cartridge 1100 according to an embodiment of the disclosure. In certain circumstances, light incident on the finger from the emitter may not be entirely absorbed by the finger. In addition, a certain portion of attenuated light will exit the other side of the finger. Such portions of light may reflect within the space between the cartridge and the finger or between the cartridge and the sensor. These portions of light can interfere with each other, with the emitted light and/or with the attenuated light. These portions of reflected light and associated interfering light can be incident on the detector. This phenomena, sometimes referred to herein as "light bounce," can potentially cause inaccurate measurements, depending on certain factors such as the amount of light bounce and the relative sensitivity of the measured signal.

The sensor cartridge 1100 is configured for application to a tissue site such as a finger, for example. The finger or other tissue site may be placed in the opening 1102. In addition, the cartridge 1100 is configured for insertion into a reusable sensor such as the sensor 120. The sensor cartridge 1100 further includes an upper aperture 1104 and a lower aperture 1106. The apertures 1104, 1106 generally allow for proper sensor operation. For example, the apertures 1104, 1106 allow for light from one or more emitters of the sensor 120 to contact the finger and for light attenuated by the tissue site to be received by a detector of the sensor 120. The apertures 1104, 1106 may function in a manner similar to and provide similar advantages as the apertures 115, 117 of the cartridge 110 of FIGS. 1-2. The cartridge may comprise Acrylonitrile Butadiene Styrene ("ABS"), other types of rubber or plastic materials, or some other material compatible with the embodiments described herein.

As shown, the sensor cartridge 1100 generally envelopes the finger when it is applied to the cartridge 1100. Moreover, the cartridge 1100 may comprise a color absorptive of the light emitted from the emitter of the sensor 120. For example, the cartridge 1100 may comprise a dark material as shown, such as a substantially black or opaque material. As described above, a certain portion of incident on the finger from the emitter of the sensor 120 may not be absorbed by the finger, but may instead be reflected off of the finger. In addition, a certain portion of attenuated light will exit the other side of the finger. Because the cartridge 1100 generally envelopes the finger and is absorptive of the emitted light, light which is not absorbed by the finger or otherwise may advantageously escape into the region between the cartridge and the finger will be substantially absorbed by the cartridge 1100 due to its absorptive properties, reducing the effect of light bounce.

Alternative configurations of the cartridge 1100 are possible as will be recognized by skilled artisans from the disclosure herein. For example, the cartridge 1100 body may comprise a substantially thin rubber material in some embodiments. The cartridge 1100 may include an adhesive proximate the perimeter of the opening 1102, such as the self-adhesive strip 820 of the cartridge 800 of FIG. 8, which may help create a seal between the finger and the cartridge 1100. In other configurations, the perimeter of the opening may include an elastic band capable of creating an elastic seal between the finger and the cartridge 1100. In certain embodiments, the cartridge 1100 or a portion thereof may include a different color such as a relatively light color, or may be translucent or partially translucent. In one configuration, the interior of the cartridge 1100 comprises a substantially dark color and the outer surface comprises another color, such as a light color. In yet another embodiment, the interior of the cartridge 110 comprises a substantially light color and the outer surface comprises a substantially dark color.

Figure 12A:
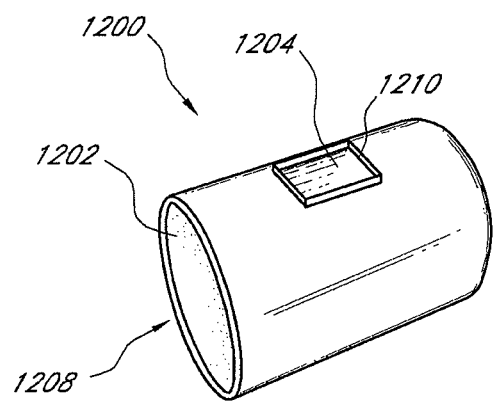
FIGS. 12A-B illustrate top front and bottom rear perspective views, respectively, of a sensor cartridge according to another embodiment of the disclosure.
Figure 12B:
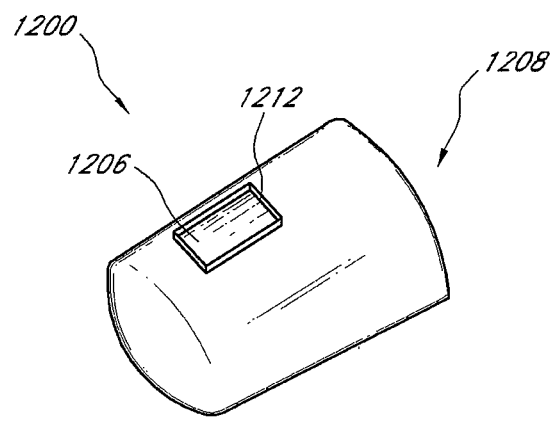

FIGS. 12A-B illustrate top front and bottom rear perspective views, respectively, of a sensor cartridge according to another embodiment of the disclosure. The cartridge 1200 of FIG. 12 may be generally similar in structure and function to the cartridge 1100 of FIG. 11. For example, the cartridge 1200 includes an opening 1202, a cavity 1208, an upper aperture 1204 and a lower aperture 1206. In addition, the cartridge 1200 comprises a color absorptive of the emitted light and advantageously reduces the effect of light bounce.

The cartridge 1200 may not fit in a uniformly snug manner with the upper and lower sensor housings 122, 124. For example, as the upper and lower sensor housings 122, 124 exert force directly on the outer surface of the cartridge 1200 and thus indirectly on the tissue site within the cartridge 1200, the sensor cartridge 1200 may flex and partially deform in response to this force. This flexing may create gaps between portions of the inner surfaces of the upper and lower sensor housings 122, 124 and the outer surface of the cartridge 1200. The cartridge 1200 includes connecting portions 1210, 1212 which are configured to bridge potential gaps between the outer surface of the cartridge 1200 and the inner surfaces of the upper and lower sensor housings 122, 124. Particularly, the connecting portions 1210, 1212 are configured to bridge these gaps substantially in the region of the perimeter of the apertures 1204, 1206, respectively. The connecting portions 1210, 1212 thereby create a seal between the perimeter of the apertures 1204, 1206 and the inner surfaces of the upper and lower sensor housings 122, 124, respectively. Channel regions are thus created whereby light from the emitter can travel from the emitter to the aperture 1204 and whereby attenuated light can travel from the tissue site to the detector. Thus, the connecting portion 1210 prevents light directed towards the upper aperture 1204 from the emitter from escaping into the region between the between the inner surface of the upper sensor housing 122 and the outer surface of the cartridge 1200. Likewise, the connecting portion 1212 prevents attenuated light exiting the tissue site towards the detector of the sensor 120 from prevented from escaping into the region between the inner surface of the lower sensor housing 124 and the cartridge 1200. Because light escaping into these regions may contribute to light bounce, as described above, the connecting portions 1210, 1212 advantageously provide further reduction of light bounce. Moreover, the connecting portions 1210, 1212 generally cause a greater percentage of light from the emitter to be directly incident on the tissue site and a cause greater percentage of attenuated light exiting from the tissue site to be directly incident on the detector. The connecting portions 1210, 1212 thus can provide for increased measurement accuracy, improved calibration and efficiency of sensor operation, among other advantages.

The connecting portions 1210, 1212 of the illustrated embodiment include four panels each extending from one side of the perimeter of the upper and lower apertures 1204, 1206 to form raised rectangular borders around the apertures 1204, 1206. The connecting portions 1210, 1212 are configured to contact the interior surfaces of the upper and lower sensor housings 122, 124 around the emitter and the detector, respectively. The connecting portions 1210, 1212 include a flexible material such as a rubber or plastic which conforms to the interior surfaces of the upper and lower sensor housings 122, 124, respectively. As such, the connecting portion 1210 helps to create a seal between the emitter of the sensor 120 and the cartridge as described above, thereby reducing light bounce and providing for increased measurement accuracy. Likewise, the connecting portion 1212 helps to create a seal between the detector of the sensor 120 and the cartridge 1200 as described above, thereby further reducing light bounce and improving measurement accuracy.

As will be appreciated by those of skill in the art from the disclosure provided herein, alternative configurations of the cartridge 1200 are possible. For example, in certain embodiments, one or more of the connecting portions 1210, 1212 may comprise a rigid material. The connecting portions 1210, 1212 may mate with corresponding features of the interior surfaces of the upper and lower sensor housings 122, 124, respectively. For example, the connecting portions 1210, 1212 may form raised features such as in the illustrated embodiment which fit into corresponding female portions, such as recesses in the interior surfaces of the sensor housings 122, 124. In various embodiments, snap-fit, friction-fit, and other mating mechanisms may be employed. Certain features may be reversed in some embodiments. For example, one or more of the interior surfaces of the sensor housings 122, 124 may include male portions and the connecting portions 1210, 1212 may include female portions. In certain embodiments, connecting portions such as the connecting portions 1210, 1212 may be used on other cartridges described herein, such as, for example, the cartridge 110 of FIGS. 1-2, or the cartridge 300 of FIG. 3.

Various sensor cartridges and covers have been disclosed in detail in connection with various embodiments. These embodiments are disclosed by way of examples only and are not to limit the scope of the claims that follow. One of ordinary skill in the art will appreciate the many variations, modifications and combinations. For example, in one embodiment, the cartridge 110 of FIG. 2 includes a securing feature such as the securing feature 311 of the cartridge 300 of FIG. 3. In some embodiments, the cartridges 110, 300 of FIGS. 2 and 3 are configured to substantially envelope the tissue site in a manner similar to the cartridges 1100, 1200 of FIGS. 11 and 12. In various embodiments, any of the cartridges described throughout the disclosure, such as the cartridges 300, 510, 610, 1100, 1200 described with respect to FIGS. 3, 5, 6, 11 and 12, may include a film covering the respective apertures. For example, the film may include a film such as the one described above with respect to the apertures 115, 117 of the cartridge 110 of FIGS. 1-2. In addition, in various embodiments the sensor cartridges and covers are used with a sensor that may measure any type of physiological parameter. In various embodiments, the sensor cartridges and covers may be for any type of medical device.

What is claimed is:

1. A disposable sterile barrier configured to interpose a material between a tissue site and surfaces of a sensor configured to grasp the tissue site, the sensor configured to transmit optical radiation into the tissue site and to generate a signal responsive to the optical radiation after attenuation by pulsatile blood flow within the tissue site, the disposable sterile barrier comprising:
   a barrier comprising a collapsible tube the barrier being made of a substantially optically transparent material;
   a first portion of the collapsible tube including an open end, wherein the first portion is sized to receive a reusable optical sensor in the collapsible tube, and wherein at least a portion of the first portion is configured to be interposed between a tissue site and a first surface of the reusable optical sensor proximate an emitter of the reusable optical sensor; and a second portion of the collapsible tube including a closed end, wherein the second portion is sized to receive the reusable optical sensor in the collapsible tube, and wherein at least a portion of the second portion is configured to be interposed between the tissue site and a second surface of the reusable optical sensor proximate a detector of the reusable optical sensor.

2. The disposable sterile barrier of claim 1, wherein:

the barrier comprising the collapsible tube is configured to be placed over the reusable optical sensor and over at least a portion of a sensor cable extending from the reusable optical sensor, and the barrier further comprises a fastener proximate the open end of the collapsible tube, the fastener configured to close the open end of the collapsible tube around the sensor cable.

3. The disposable sterile barrier according to claim 2, wherein the collapsible tube is capable of accommodating a first sensor housing comprising one of the first and second surfaces and to accommodate a second sensor housing comprising the other of the first and second surfaces so as to enclose the reusable optical sensor within the collapsible tube.

4. The disposable sterile barrier of claim 1, wherein the tissue site is at least a portion of a finger.

5. An optical sensing method of non-invasively measuring constituents of pulsatile blood flow within a tissue site without substantial risk of nosocomial infection by direct contact between a reusable optical sensor and the tissue site, the optical sensing method comprising:

providing a reusable optical sensor having an emitter disposed within a first housing and a detector disposed within a second housing, the emitter and detector in communication with a sensor cable, the first and second housings configured to be urged against opposite sides of a tissue site upon application of the reusable optical sensor to the tissue site, the emitter configured to transmit optical radiation having one or more predetermined wavelengths into the tissue site and the detector configured to receive the optical radiation after attenuation by the tissue site, the reusable optical sensor configured to generate one or more signals indicative of the attenuated radiation, the one or more signals transmitted via the sensor cable to a monitor configured to process the one or more signals to determine one or more physiological parameters of a patient; and applying a barrier so as to make physiological measurements without direct contact between the tissue site and the reusable optical sensor, the barrier configured to be interposed between the tissue site and the first housing and configured to be interposed between the tissue site and the second housing upon application of the tissue site to the reusable optical sensor, the barrier comprising material substantially transparent so as not to substantially distort the physiological measurements, the barrier further comprising a collapsible tube comprising a first portion and a second portion, the first portion comprising an open end and sized to receive the reusable optical sensor, the second portion comprising a closed end and sized to receive the reusable optical sensor.

6. The optical sensing method of claim 5, further comprising disposing of the barrier after determining one or more physiological parameters of the patient.

7. The optical sensing method of claim 5, wherein applying further comprises:

providing the barrier comprising the collapsible tube;

expanding the collapsible tube from a collapsed state to an un-collapsed state;

fitting the open end of the collapsible tube around one of the first sensor housing and the second sensor housing;

moving the open end firstly along one of the first and second housings and then along the other of the first and second housings such that the reusable optical sensor and at least a portion of the sensor cable are enclosed within the tube; and sealing the open end around the sensor cable.

8. The optical sensing method of claim 5, wherein the tissue site is at least a portion of a finger.

9. A disposable sterile barrier comprising:

an elongate tube comprising a cavity, an open end and a closed end, the open end comprising an opening large enough to accommodate a reusable optical sensor, the cavity sized to fully enclose the reusable optical sensor and at least a portion of a sensor cable extending from the optical sensor, the elongate tube comprising a material which is substantially optically transparent; and a fastener disposed proximate the open end of the elongate tube and configured to seal the open end of the elongate tube around the sensor cable.

* * * * *